(12) United States Patent
Hegde

(10) Patent No.: US 8,486,651 B2
(45) Date of Patent: Jul. 16, 2013

(54) METHOD FOR TREATING A DISORDER ASSOCIATED WITH EYA DYSREGULATION BY MODULATING EYA PHOSPHATASE ACTIVITY

(75) Inventor: Rashmi Hegde, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 13/133,593

(22) PCT Filed: Dec. 8, 2009

(86) PCT No.: PCT/US2009/067220
§ 371 (c)(1),
(2), (4) Date: Aug. 29, 2011

(87) PCT Pub. No.: WO2010/077693
PCT Pub. Date: Jul. 8, 2010

(65) Prior Publication Data
US 2011/0312918 A1     Dec. 22, 2011

Related U.S. Application Data

(60) Provisional application No. 61/120,564, filed on Dec. 8, 2008.

(51) Int. Cl.
*C12Q 1/42*     (2006.01)
(52) U.S. Cl.
USPC .......................................................... 435/21
(58) Field of Classification Search
USPC .......................................................... 435/21
See application file for complete search history.

(56) References Cited

U.S. PATENT DOCUMENTS
2007/0156343 A1     7/2007     Rayan

FOREIGN PATENT DOCUMENTS
WO     WO 2010/077693     7/2010

OTHER PUBLICATIONS

Krueger A. et al. Identification of a Selective Small Molecule Inhibitor Series . . . J of Biomolecular Screening 1-12, Jul. 20, 2012.*
Tootle T. et al. The Transcription Factor Eyes Absent Is a Protein Tyrosine Phosphatase. Nature 426:299-302, 2003.*
Tadjuidje E. et al. The Eya Tyrosine Phosphatase Activity is Proangiogenic and is Inhibited by Benzbromarone. PLoS One 7(4)e34806, 2012.*
Jemc J. et al. The Eyes Absent Family . . . Annual Review of Biochemistry 76(1)513-538, Jul. 2007.*
PCT International Preliminary Report on Patentability in corresponding International application No. PCT/US2009/067220, mailed on Jun. 23, 2011, 7 pages.
Bonini, et al., "The eyes absent gene: genetic control of cell survival and differentiation in the developing Drosophila eye," Cell, vol. 72(3), p. 379-395, 1993.
Bonini, et al., Development, "The eyes absent gene: genetic control of cell survival and differentiation in the developing Drosophila eye," vol. 124(23), p. 4819-4826, 1997.
Coletta, et al., "The Six1 homeoprotein stimulates tumorigenesis by reactivation of cyclin A1," Proc. Natl. Acad. Sci., vol. 101(17), p. 6478-6483, 2004.
Easty, et al., "Protein Tyrosine Phosphatases, New Targets for Cancer Therapy," Curr. Cancer Drug Targets, vol. 6(6), p. 519-532, 2006.
Ford, et al., "Abrogation of the G2 cell cycle checkpoint associated with overexpression of HSIX1: A possible mechanism of breast carcinogenesis," Proc. Natl. Acad. Sci., vol. 95(21), p. 12608-12613, 1998.
Ford, et al., "Cell Cycle-regulated Phosphorylation of the Human SIX1 Homeodomain Protein," J. Biol. Chem., vol. 275(29), p. 22245-22254, 2000.
Ghose, et al., "A knowledge-based approach in designing combinatorial or medicinal chemistry libraries for drug discovery. 1. A qualitative and quantitative characterization of known drug databases," J. Comb.Chem. , vol. 1, p. 55-68, 1999.
Hazbun, et al., "Site-Specific Recognition by Isolated DNA-Binding Domain of the Sine Oculis Protein," *Biochemistry* 36:3680-3686, 1997.
Hennipman, et al., "Tyrosine Kinase Activity in Breast Cancer, Benign Breast Disease, and Normal Breast Tissue," Cancer Res., vol. 49(3): 516-521, 1989.
Hu, et al., "DNA-Binding and Regulation Mechanisms of the SIX Family of Retinal Determination Proteins." *Biochemistry* 47(11):3586-3594, 2008.
Kaiser, et al., 2007. "Exclusion of genes from the EYA-DACH-SIX-PAX pathway as candidates for Branchio-Oculo-Facial syndrome (BOFS)." *American Journal of Medical Genetics Part A* 143A(18):2185-2188.
Kohler and Milstein, "Continuous cultures of fused cells secreting antibody of predefined specificity," Nature, vol. 256, p. 495-497, 1975.
Laflamme, et al., 2003. "The Homeotic Protein Six3 Is a Coactivator of the Nuclear Receptor NOR-1 and a Corepressor of the Fusion Protein EWS/NOR-1 in Human Extraskeletal Myxoid Chondrosarcomas [1]" *Cancer Research* 63(2): 449-454.
Lipinski, et al., "Experimental and computational approaches to estimate solubility and permeability in drug discovery and development settings," Adv. Drug Del. Rev., vol. 46, p. 3-26, 2001.
Miller, et al., "Inhibition of Eyes Absent Homolog 4 expression induces malignant peripheral nerve sheath tumor necrosis," Oncogene, vol. 29(3), p. 368-379, Epub 2009.

(Continued)

*Primary Examiner* — Ralph Gitomer
(74) *Attorney, Agent, or Firm* — Davis Wright Tremaine LLP

(57) ABSTRACT

The present invention provides a novel mechanistic pathway and methods related to this pathway for the identification of compounds for the treatment of diseases involving cell proliferation, invasion and/or metastasis such as cancer. In particular, the instant invention relates to the phosphatase activity of Eya and the Eya-Six complex as a target for identifying novel therapeutic agents for the treatment of proliferative, invasive and/or metastatic disorders, and compositions identified using the methods disclosed herein.

11 Claims, 9 Drawing Sheets

OTHER PUBLICATIONS

Musharraf, et al., 2008. "Eyes Absent Proteins: Characterization of Substrate Specificity and Phosphatase Activity of Mutants Associated with Branchial, Otic and Renal Anomalies" *ChemBioChem* 9(14):2285-2294.

Nicolson, et al., "Transfilter Cell Invasion Assays, 3rd ed.," Cell Biology: A Laboratory Handbook, Elsevier Academic Press, pp. 359-362, 2006.

Ohto, et al., "Cooperation of Six and Eya in Activation of Their Target Genes through Nuclear Translocation of Eya," Mol. Cell. Bio., vol. 19, p. 6815-6824, 1999.

Ottenhoff-Kalff, et al., "Protein tyrosine phosphatase activity as a diagnostic parameter in breast cancer," Breast Cancer Res. Treat., vol. 33(3), p. 245-256, 1995.

Rayapureddi, et al., "Eyes absent represents a class of protein tyrosine phosphatases," Nature, vol. 426, p. 295-298, 2003.

Rayapureddi, et al, "Characterization of a plant, tyrosine-specific phosphatase of the aspartyl class," Biochemistry, vol. 44(2), p. 751-758, 2005.

Rayapureddi and Hegde, "Branchio-oto-renal syndrome associated mutations in Eyes Absent 1 result in loss of phosphatase activity," FEBS Lett., vol. 580(16), p. 3853-3859, 2006.

Sjoblom, et al., "The Consensus Coding Sequences of Human Breast and Colorectal Cancers," Science, vol. 314(5797), p. 268-274, 2006.

Tootle, et al., "The transcription factor Eyes absent is a protein tyrosine phosphatase," Nature, vol. 426(6964), p. 299-302, 2003.

Walters, et al., "Virtual screening—an overview," Drug Discovery Today, vol. 3, p. 160-178, 1998.

Xu and Stevenson, "Drug-like index: a new approach to measure drug-like compounds and their diversity," J. Chem. Inf. Comput. Sci., vol. 40(5), p. 1177-1187, 2000.

Yu, et al., "Expression profiling identifies the cytoskeletal organizer ezrin and the developmental homeoprotein Six-1 as key metastatic regulators," Nat. Med., vol. 10(2), p. 175-181, 2004.

Zhang, et al., "A Simple Statistical Parameter for Use in Evaluation and Validation of High Throughput Screening Assays," J. Biomol. Screen., vol. 4(2), p. 67-73, 1999.

Zhang, et al., "Transcriptional Coactivator *Drosophila* Eyes Absent Homologue 2 Is Up-Regulated in Epithelial Ovarian Cancer and Promotes Tumor Growth," Cancer Res., vol. 65(3), p. 925-932, 2005.

\* cited by examiner

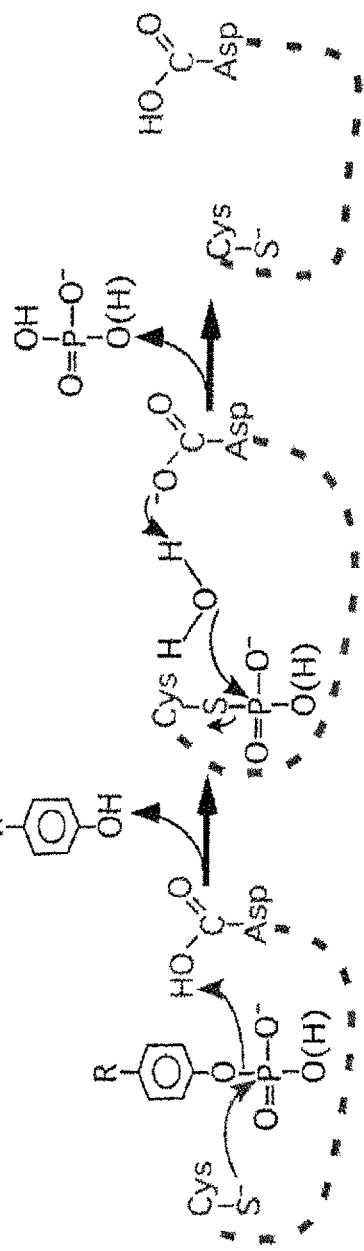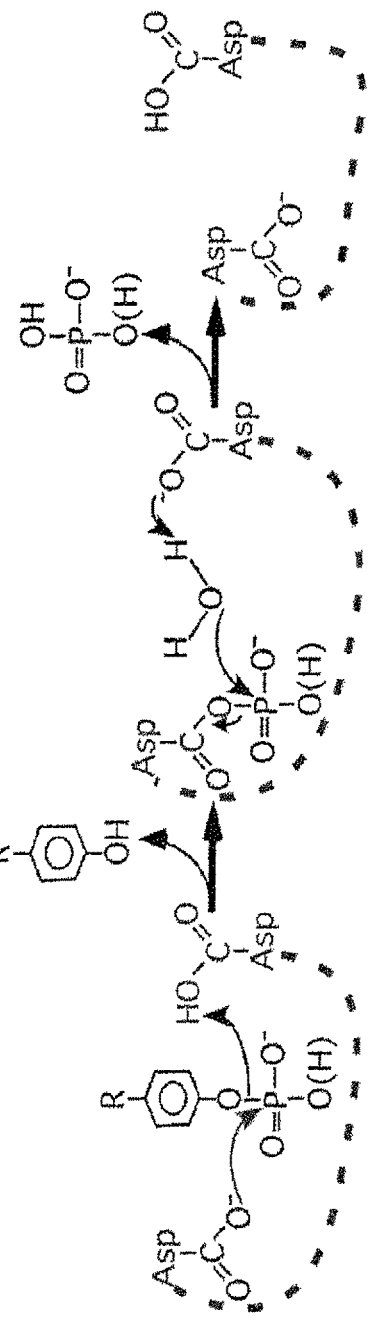
Fig. 3

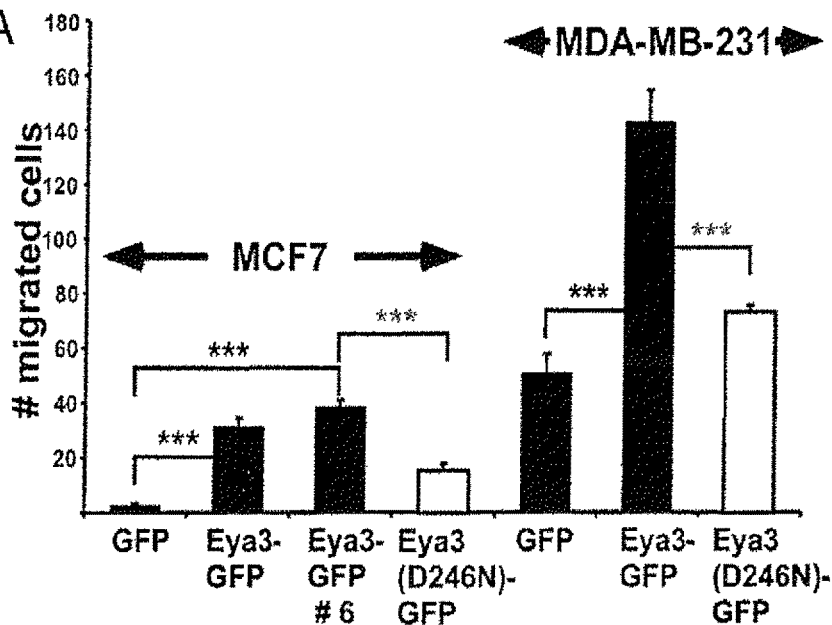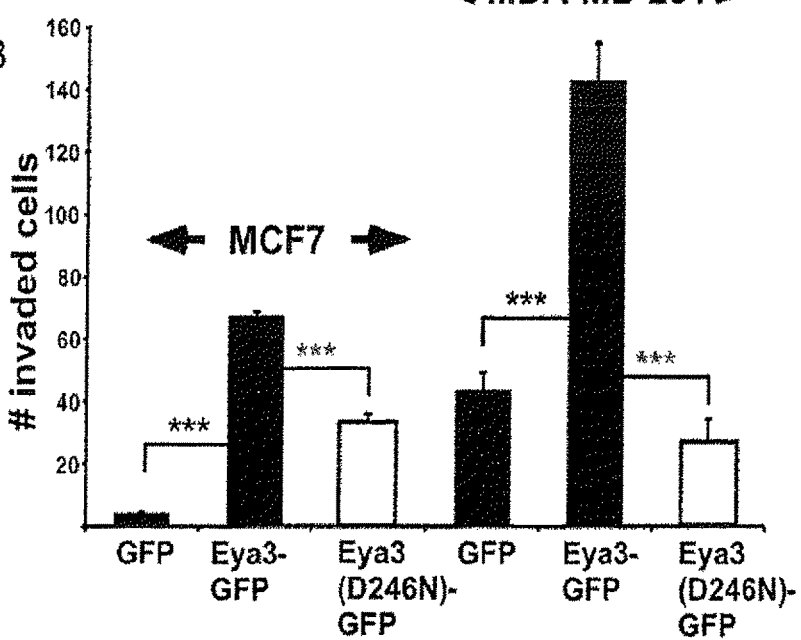

Fig 6.
A)
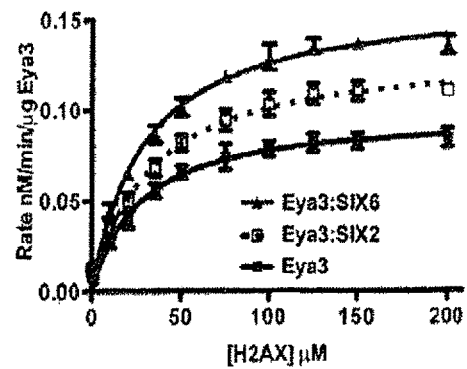
B)
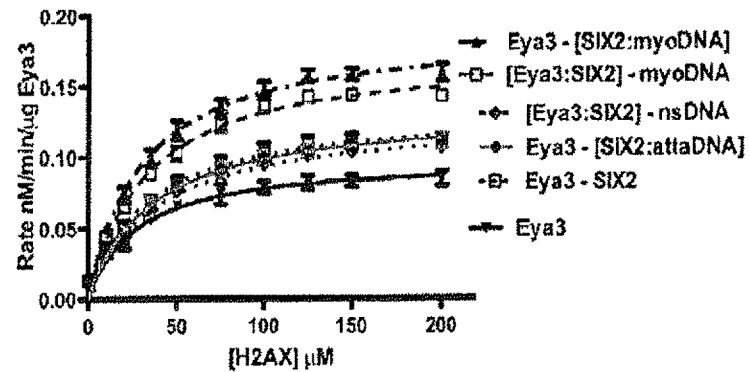
C)
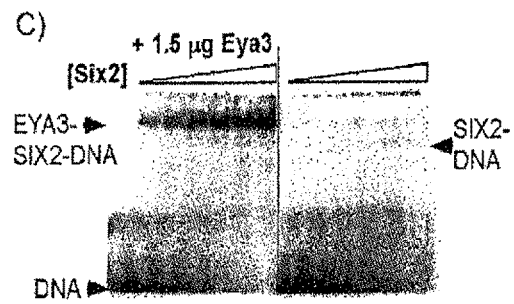

SEQUENCE LISTING

```
<160> NUMBER OF SEQ ID NOS: 9

<210> SEQ ID NO 1
<211> LENGTH: 13
<212> TYPE: DNA
<213> ORGANISM: Unknown
<220> FEATURE:
<223> OTHER INFORMATION: "ARE" regulatory element of the Na+/K+ ATPase
      alpha-1 subunit gene

<400> SEQUENCE: 1
ggtgtcaggt tgc                                                          13

<210> SEQ ID NO 2
<211> LENGTH: 13
<212> TYPE: DNA
<213> ORGANISM: Artificial Sequence
<220> FEATURE:
<223> OTHER INFORMATION: Consensus minimum binding sequence for the
      "ARE" regulatory element of the Na+/K+ ATPase alpha-1
      subunit gene
<220> FEATURE:
<221> NAME/KEY: misc_feature
<222> LOCATION: 3
<223> OTHER INFORMATION: n = A,T,C or G
<220> FEATURE:
<221> NAME/KEY: misc_feature
<222> LOCATION: 5
<223> OTHER INFORMATION: n = A,T,C or G
<220> FEATURE:
<221> NAME/KEY: misc_feature
<222> LOCATION: 7
<223> OTHER INFORMATION: n = A,T,C or G

<400> SEQUENCE: 2
ggngncnggt tgc                                                          13

<210> SEQ ID NO 3
<211> LENGTH: 7
<212> TYPE: DNA
<213> ORGANISM: Artificial Sequence
<220> FEATURE:
<223> OTHER INFORMATION: MEF3 motif

<400> SEQUENCE: 3 tcaggtt                                                                  7

<210> SEQ ID NO 4
<211> LENGTH: 7
<212> TYPE: DNA
<213> ORGANISM: Artificial Sequence
<220> FEATURE:
<223> OTHER INFORMATION: Consensus Trex/MEF3 sequence
<220> FEATURE:
<221> NAME/KEY: misc_feature
<222> LOCATION: 3
<223> OTHER INFORMATION: n = G or A
<220> FEATURE:
<221> NAME/KEY: misc_feature
<222> LOCATION: 7
<223> OTHER INFORMATION: n = G or T

<400> SEQUENCE: 4 tcnggtn                                                                  7
```

```
<210> SEQ ID NO 5
<211> LENGTH: 6
<212> TYPE: DNA
<213> ORGANISM: Artificial Sequence
<220> FEATURE:
<223> OTHER INFORMATION: Binding sequence for the sine oculis HD
<220> FEATURE:
<221> NAME/KEY: misc_feature
<222> LOCATION: 1
<223> OTHER INFORMATION: n = C or T

<400> SEQUENCE: 5 ngatac                                                                        6

<210> SEQ ID NO 6
<211> LENGTH: 296
<212> TYPE: PRT
<213> ORGANISM: Artificial Sequence
<220> FEATURE:
<223> OTHER INFORMATION: Six2 fragment from mouse Six protein

<400> SEQUENCE: 6
```

Met Ser Met Leu Pro Thr Phe Gly Phe Thr Gln Glu Gln Val Ala Cys
 1               5                  10                  15

Val Cys Glu Val Leu Gln Gln Gly Gly Asn Ile Glu Arg Leu Gly Arg
            20                  25                  30

Phe Leu Trp Ser Leu Pro Ala Cys Glu His Leu His Lys Asn Glu Ser
        35                  40                  45

Val Leu Lys Ala Lys Ala Val Val Ala Phe His Arg Gly Asn Phe Arg
    50                  55                  60

Glu Leu Tyr Lys Ile Leu Glu Ser His Gln Phe Ser Pro His Asn His
65                  70                  75                  80

Ala Lys Leu Gln Gln Leu Trp Leu Lys Ala His Tyr Ile Glu Ala Glu
                85                  90                  95

Lys Leu Arg Gly Arg Pro Leu Gly Ala Val Gly Lys Tyr Arg Val Arg
            100                 105                 110

Arg Lys Phe Pro Leu Pro Arg Ser Ile Trp Asp Gly Glu Glu Thr Ser
        115                 120                 125

Tyr Cys Phe Lys Glu Lys Ser Arg Ser Val Leu Arg Glu Trp Tyr Ala
    130                 135                 140

His Asn Pro Tyr Pro Ser Pro Arg Glu Lys Arg Glu Leu Ala Glu Ala
145                 150                 155                 160

Thr Gly Leu Thr Thr Thr Gln Val Ser Asn Trp Phe Lys Asn Arg Arg
                165                 170                 175

Gln Arg Asp Arg Ala Ala Glu Ala Lys Glu Arg Glu Asn Ser Glu Asn
            180                 185                 190

Ser Asn Ser Ser Ser His Asn Pro Leu Ala Ser Ser Leu Asn Gly Ser
        195                 200                 205

Gly Lys Ser Val Leu Gly Ser Ser Glu Asp Glu Lys Thr Pro Ser Gly
    210                 215                 220

Thr Pro Asp His Ser Ser Ser Ser Pro Ala Leu Leu Leu Ser Pro Pro
225                 230                 235                 240

Pro Pro Pro Gly Leu Pro Ser Leu His Ser Leu Gly His Pro Pro Gly
                245                 250                 255

Pro Ser Ala Val Pro Val Pro Val Pro Gly Gly Gly Ala Asp Pro
            260                 265                 270

```
Leu Gln His His His Ser Leu Gln Asp Ser Ile Leu Asn Pro Met Ser
        275                 280                 285

Ala Asn Leu Val Asp Leu Gly Ser
    290                 295

<210> SEQ ID NO 7
<211> LENGTH: 10
<212> TYPE: PRT
<213> ORGANISM: Artificial Sequence
<220> FEATURE:
<223> OTHER INFORMATION: histone H2AX C-terminus peptide
<220> FEATURE:
<221> NAME/KEY: PHOSPHORYLATION
<222> LOCATION: 9

<400> SEQUENCE: 7

Lys Lys Ala Thr Gln Ala Ser Gln Glu Tyr
 1               5                   10

<210> SEQ ID NO 8
<211> LENGTH: 12
<212> TYPE: DNA
<213> ORGANISM: Artificial Sequence
<220> FEATURE:
<223> OTHER INFORMATION: primer containing the myogenin sequence

<400> SEQUENCE: 8
tgtcaggttg ct                                                         12

<210> SEQ ID NO 9
<211> LENGTH: 12
<212> TYPE: DNA
<213> ORGANISM: Artificial Sequence
<220> FEATURE:
<223> OTHER INFORMATION: primer containing an ATTA sequence

<400> SEQUENCE: 9
tgtggattag ct                                                         12
```

US 8,486,651 B2

METHOD FOR TREATING A DISORDER ASSOCIATED WITH EYA DYSREGULATION BY MODULATING EYA PHOSPHATASE ACTIVITY

CROSS REFERENCE TO RELATED APPLICATIONS

This application is a U.S. National Stage entry under 35 U.S.C. §371 of International Application No. PCT/US2009/067220, filed Dec. 8, 2009, designating the United States of America and published in English on Jul. 8, 2010, which in turn claims the benefit of priority under 35 U.S.C. §119(e) to U.S. Provisional Application Ser. No. 61/120,564, filed on Dec. 8, 2008, entitled METHOD FOR IDENTIFYING AGENTS FOR INHIBITING CELL PROLIFERATION, which is incorporated herein by reference in its entirety.

GOVERNMENT RIGHTS

This invention was made with government support under EY014648 and EY019125 awarded by the National Institutes of Health. The government has certain rights in the invention.

BACKGROUND

The molecular pathways involved in proliferative disorders and oncogenesis often represent aberrations of processes that normally occur during embryogenesis. One such pathway implicated in proliferative disorders such as cancer is the evolutionarily conserved gene network termed the retinal determination gene network, or "RDGN."

The Six and Eya families of genes are frequently found upregulated in cancers. However, the molecular mechanisms by which the protein products of these genes might effect cancer development or progression has not been sufficiently described to allow the identification of novel therapeutics that can be used to treat proliferative disorders such as cancer. As such, current methods of measuring Eya activity and the effect of this protein on cell proliferation, migration and growth have not been successfully used to identify novel molecules for treatment of proliferative disorders.

The Eya protein, a member of the RDGN, has been shown to be a protein tyrosine phosphatase (PTP). While PTPs in general are emerging as important new targets for cancer therapy (reviewed in 15), PTPs as a target have limitations that confound the practical utility of this approach. Because PTPs share a common, thiol-based mechanism, the design of PTP inhibitors has been hampered by the inability to achieve specificity among the large family of mammalian PTPs. Due to the conserved regions of the active site among PTPs, particularly the conserved catalytic cysteine residue, targeting specific PTPs has proved difficult. Furthermore, most potent PTP inhibitors identified to date tend to be phospho-tyrosine mimics that have poor cell-permeability and other pharmaceutical properties, thus making them unsuitable for effective therapeutic use in treating proliferative disorders.

Anti-vascular therapy has emerged as an extremely promising option for the treatment of several major diseases including solid tumors and the vision-compromising ailments diabetic retinopathy, age-related macular degeneration (AMD) and retinopathy of prematurity. The protein tyrosine phosphatases (PTPs) of the Eyes Absent family are highly likely to be useful drug targets in anti-vascular therapy. Eyes Absent phosphatases are expressed in vascular endothelial cells (VECs) and the phosphatase activity enhances cell migration and the formation of vessel-like structures in culture.

Agents that specifically target PTPs have enormous potential in the treatment of proliferative, invasive and/or metastatic, angiogenic and/or vascular disorders such as cancer, given the significant increase in PTP activity in many disease states. Though approximately 30% of cellular proteins are phospho-proteins, tyrosine phosphorylation accounts for only about 0.01% to about 0.05% of all phospho-proteins. In disease states such as oncogenic transformation, however, tyrosine phosphorylation is increased up to one to two hundred-fold to 1 to 2% of the total phospho-protein population. While protein tyrosine phosphatases have been extensively linked with disease states including proliferative diseases such as cancer, the design of tyrosine phosphatase inhibitors, as discussed above, has traditionally been confounded by a lack of specificity, and there remains a significant need in identifying PTP specific inhibitors for the treatment of disorders involving PTP dysregulation.

Thus, there exists a need in the art for inhibitors with no inhibitory activity toward the large family of classical PTPs. The methods of the instant invention seek to address this limitation in the art.

SUMMARY

The present invention relates to a novel synergistic interaction between the Six proteins and Eyes Absent (Eya) proteins.

Embodiments of the invention relate to a method of identifying a potential therapeutic agent for the treatment of a disorder associated with Eyes Absent (Eya) dysregulation and include the steps of: i) providing an Eya protein or fragment, wherein the Eya protein or fragment possesses relevant biochemical activity, and a substrate capable of being dephosphorylated by the Eya protein or fragment; ii) introducing a test molecule to the Eya protein or fragment; iii) determining the effect of the test molecule on the phosphatase activity of the Eya protein or fragment; iv) comparing the phosphatase activity of the Eya protein or fragment in the presence of a test molecule to that of a reference standard; wherein a test molecule that increases or decreases Eya phosphatase activity is a potential therapeutic agent for the treatment of a proliferative disorder.

In some embodiments, a method for identifying a potential therapeutic agent for the treatment of a disorder associated with Eyes Absent dysregulation, include the steps of: i) providing an Eya and Six protein or fragment, wherein the Eya and Six protein or fragment possesses relevant biochemical activity, and a substrate capable of being dephosphorylated by the Eya protein or fragment; ii) introducing a test molecule to the Eya and Six protein or fragment; iii) determining the effect of the test molecule on the phosphatase activity of the Eya protein or fragment; iv) comparing the phosphatase activity of the Eya protein or fragment in the presence of a test molecule to that of a reference standard; wherein a test molecule that increases or decreases Eya phosphatase activity is a potential therapeutic agent for the treatment of a proliferative disorder.

In other embodiments, the disorder associated with Eya dysregulation include, for example, a proliferative disorder and the like, an invasive and/or metastatic disorder and the like, an angiogenic disorder and the like, a vascular disorder and the like, and cancer and the like.

In some embodiments, the Eya protein can be, for example, Eya1, Eya2, Eya3, Eya4, and the like.

In alternative embodiments, the fragment includes the Eya domain (ED) region of an Eya protein, wherein the Eya protein can include, for example, Eya1, Eya2, Eya3, Eya4, and the like.

In other embodiments, the Six protein can be, for example, Six1, Six2, Six3, Six4, Six5, Six6, and the like.

In other embodiments, the substrate can be, for example, the model substrate pNPP, phospho-amino acids, phosphorylated peptides, phosphorylated proteins, and the like.

In some embodiments, a method for identifying a potential therapeutic agent for the treatment of a proliferative, invasive and/or metastatic, angiogenic and/or vascular disorder, include the steps of: i) providing an Eya protein or fragment, wherein the Eya protein or fragment possesses measurable tyrosine phosphatase activity, and a substrate capable of being dephosphorylated by the Eya protein or fragment under conditions that permit Eya phosphatase activity; ii) introducing a test molecule to the Eya protein or fragment; iii) determining the phosphatase activity of the Eya protein or fragment; iv) comparing the phosphatase activity of the Eya protein or fragment in the presence of a test molecule to that of a reference standard; wherein a molecule capable of inhibiting Eya phosphatase activity are identified as a candidate compound for the treatment of a proliferative, invasive and/or metastatic disorder, angiogenic and/or vascular disorder.

In alternative embodiments, a method for identifying a potential therapeutic agent for the treatment of a proliferative, invasive and/or metastatic, angiogenic or vascular disorder, include the steps of: i) providing an Eya and Six protein or fragment, wherein the Eya protein or fragment possesses measurable tyrosine phosphatase activity and the Six protein or fragment is capable of interacting with the Eya protein or fragment, and a substrate capable of being dephosphorylated by the Eya protein or fragment under conditions that permit Eya phosphatase activity; ii) introducing a test molecule to the Eya and Six protein or fragment; iii) determining the phosphatase activity of the Eya protein or fragment; iv) comparing the phosphatase activity of the Eya protein or fragment in the presence of a test molecule to that of a reference standard; wherein a molecule capable of inhibiting Eya phosphatase activity are identified as a candidate compound for the treatment of a proliferative, invasive and/or metastatic, angiogenic and/or vascular disorder.

In other embodiments, a composition for the treatment of a proliferative disorder and the like, an invasive and/or metastatic disorder and the like, an angiogenic and/or vascular disorder and the like is identified using the above described methods.

In some embodiments, a method of treating, for example, a proliferative disorder and the like, in a patient by administering to an individual suspected of having a proliferative disorder and the like, a therapeutically effective amount of a compound that inhibits, for example, Eya's phosphatase activity. In other embodiments, a method of treating, for example, an invasive and/or metastatic disorder and the like, in a patient by administering to an individual suspected of having a invasive and/or metastatic disorder and the like, a therapeutically effective amount of a compound that inhibits, for example, Eya's phosphatase activity and the like. In an alternative embodiment, a method of treating, for example, an angiogenic and/or vascular disorder and the like, in a patient by administering to an individual suspected of having a angiogenic and/or vascular disorder and the like, a therapeutically effective amount of a compound that inhibits, for example, Eya's phosphatase activity and the like.

In some embodiments a method of treating, for example, a proliferative disorder and the like, in a patient by administering to an individual suspected of having, for example, a proliferative disorder and the like, a therapeutically effective amount of a compound that inhibits the interaction between, for example, Six and Eya and the like or that, for example, alters Eya's phosphatase activity in the presence of, for example, the Six proteins and the like. In other embodiments, a method of treating, for example, an invasive and/or metastatic disorder and the like, in a patient by administering to an individual suspected of having, for example, an invasive and/or metastatic disorder and the like, a therapeutically effective amount of a compound that inhibits the interaction between, for example, Six and Eya and the like or that, for example, alters Eya's phosphatase activity in the presence, for example, of the Six proteins and the like.

In some embodiments a method of treating, for example, an angiogenic and/or vascular disorder and the like, in a patient by administering to an individual suspected of having, for example, an angiogenic and/or vascular disorder and the like, a therapeutically effective amount of a compound that inhibits, for example, the interaction between, for example, Six and Eya and the like or that, for example, alters Eya's phosphatase activity in the presence of, for example, the Six proteins and the like.

BRIEF DESCRIPTION OF THE FIGURES

Exemplary embodiments are illustrated in referenced figures. It is intended that the embodiments and figures disclosed herein are to be considered illustrative rather than restrictive.

FIG. 3 is a schematic of the mechanism of action of classical Protein Tyrosine Phosphatase (PTPs) (a) and the EYA family of PTPs (b). The phosphatase activity of PTPs generally proceeds through a thiol-based mechanism, wherein a cysteine residue is the nucleophile. The Eyes Absent phosphatases use a reaction mechanism with aspartate as a nucleophile.

FIG. 5 is a graph of in vitro cell migration and invasion demonstrating that cells overexpressing Eya3 have increased motility and invasiveness and that the phosphatase activity of Eya promotes cell migration and invasion. (A) Cell migration of MCF-7 or MDA-MD-231 cells over-expressing either GFP, Eya3-GFP, Eya3-GFP #6 or Eya3(D246N)-GFP, a phosphatase deficient variant of Eya (gray bar), was measured. (D246N-mutation from aspartic acid to asparagine at amino acid position 246 of Eya3). The number of cells migrating to the bottom side of a transwell insert are indicated (mean of three experiments+SD, * $p<0.001$,  $p<0.01$, * $p<0.05$). (B) The invasiveness of cells over-expressing Eya3 was measured using a Matrigel® invasion assay. The invasion assays were performed, as described in 5(A), except that the transwells were coated with basement membrane Matrigel® and the cells migrating to the bottom side of the insert were measured 48 hours after the start of the experiment. Each bar represents the mean of three experiments±SD, * p<0.001,  p<0.01, * p<0.05.

FIG. 6 shows that interaction of Eya with SIX2, SIX6 and SIX2-DNA, increases the catalytic activity of Eya3 towards a peptide representing its substrate H2AX. (A) The ability of Eya3 to dephosphorylate a tyrosine-phosphorylated peptide derived from H2AX was monitored in the presence or absence of stoichiometric amounts of either SIX2 or SIX6. The catalytic rate at increasing concentrations of H2AX-pY peptide was measured. The results show that the interaction with these SIX proteins increases the $k_{cat}$ of Eya3, while the $K_m$ values remain relatively similar. In control experiments, neither SIX2 nor SIX6 showed any catalytic activity, and the presence of SIX2 or SIX6 did not alter the inability of Eya3 to dephosphorylate either pNPP or pY. (B) Localization of the EYA phosphatase on DNA via the SIX proteins is likely to be an entropic advantage as well as providing a means by which PTP can act upon a DNA-wrapped substrate protein. In order to confirm that an EYA-SIX-DNA complex retained activity and the specificity observed for the SIX-EYA complex, the phosphatase activity of EYA was measured in the presence or absence of a DNA sequence known to be specifically bound by SIX2. SIX2 specifically binds to the TCAGGTT, a sequence present in the myogenin promoter. The catalytic activity of Eya3 to dephosphorylate H2AX, alone or in a complex of Eya3:SIX2, was measured in the presence of an oligonucleotide with the myogenin sequence (TG TCAGGTTGCT; myoDNA), a related sequence lacking the SIX2 binding motif (TGTGGATTAGCT; attaDNA), or a completely unrelated DNA sequence (nsDNA). The presence of DNA increased the phosphatase activity of Eya3 and was relatively on the presence of the myogenin sequence. The order of addition had a consistent impact on the phosphatase activity of Eya. Interaction of a pre-formed SIX:myoDNA complex (Eya3-[SIX2:myoDNA]) resulted in a higher catalytic rate relative to when an Eya3:SIX2 complex was mixed with myoDNA [Eya3:SIX2]-myoDNA. (C) an electrophoretic mobility shift assay using a DNA probe containing the myogenin promoter (a Six2 target) and increasing concentrations of Six2 alone (right half of gel) or Six2 in the presence of Eya3(ED) (left half).

DESCRIPTION

Definitions

Figure 1:
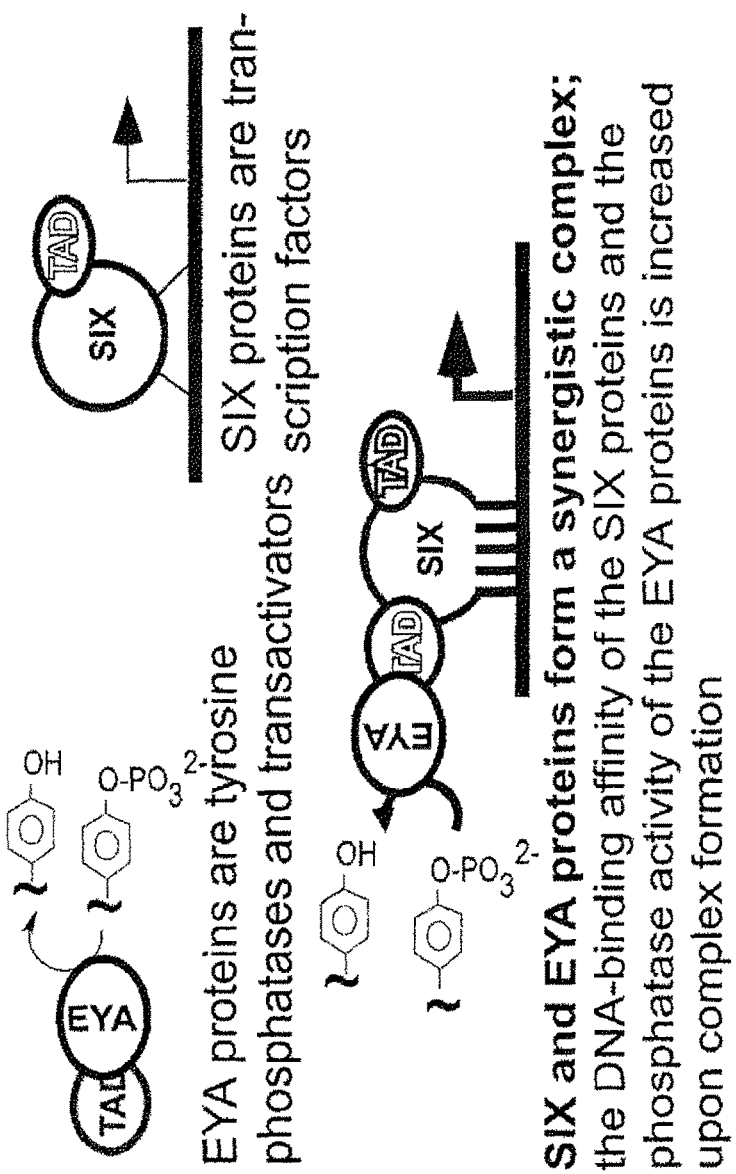
FIG. 1 is a schematic of the proposed molecular mechanisms of the Six and Eya proteins.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sam brook and Russell, *Molecular Cloning: A laboratory Manual* 3$^{rd}$ ed., Cold Spring Harbor Laboratory Press (Cold Spring Harbor, N.Y. 2001), provide one skilled in the art with a general guide to many terms used in the present application.

As used herein, the terms "therapy" and "therapies" refer to, in some embodiments, to any method, protocol and/or agent that can be used in the prevention of a disease or disorder or one or more symptoms thereof. In some embodiments, the terms therapy and therapies refer to any method, protocol and/or agent that can be used in the management of a disease or a disorder or one or more symptoms thereof. In other embodiments, the terms therapy and therapies refer to any method, protocol and/or agent, that can be used in the amelioration of a disease or a disorder or one or more symptoms thereof.

As used herein, the term "therapeutically effective amount" refers to, in some embodiments, an amount of a therapy, for example, a therapeutic agent sufficient to result in the amelioration of one or more symptoms of a disorder. In other embodiments, a therapeutically effective amount refers to an amount of therapy, for example, a therapeutic agent sufficient to prevent advancement of a disorder. In other embodiments, a therapeutically effective amount refers to an amount of therapy, for example, a therapeutic agent sufficient to cause regression of a disorder. In other embodiments, a therapeutically effective amount refers to an amount of a therapy, for example, a therapeutic agent sufficient to enhance or improve the therapeutic effect(s) of another therapy.

As used herein, the term "therapeutic agent" refers to a compound that provides a desired biological or pharmacological effect when administered to a human or animal. The therapeutic agent can be a small molecule, for example. The therapeutic agent can also be a protein, an antibody, a mimetibody, a peptide, an enzyme, a nucleotide, a DNA fragment, a RNA fragment, a plasmid fragment, or a nucleotide fragment, or mixtures thereof. The term "potential therapeutic agent," as used herein, refers to an agent that will be recognized as having the potential in vivo, in some embodiments, to reduce at least one symptom of a disorder associated with Eyes Absent dysregulation. In some embodiments, a potential therapeutic agent refers to any candidate agent that will be recognized as having the potential in vivo to alleviate at least one symptom of a disorder associated with Eyes Absent dysregulation. In some embodiments, a potential therapeutic agent refers to any candidate agent that will be recognized as having the potential in vivo to prevent at least one symptom of a disorder associated with Eyes Absent dysregulation. In some embodiments, a potential therapeutic agent refers to any candidate agent that will be recognized as having the potential in vivo to prevent at least one symptom of a disorder associated with Eyes Absent dysregulation. In other embodiments, a potential therapeutic agent refers to any candidate agent that is determined to have an in vitro effect on test cells. The measured effect can vary, but can include, for example, inhibition of viability, or growth, or proliferation, or migration of test cells and the like. Potential therapeutic agents, as used herein, are identified as having a desired effect in vitro, and are considered "hits" which can be subjected to further in vitro or in vivo evaluation to determine or optimize the therapeutic benefit, or, alternatively, can be used to identify derivative or analogous agents which can in turn be evaluated for an in vitro or in vitro therapeutic effect.

As used herein, the term "increase" refers to an enhanced level of measurable polypeptide activity in a given assay in the presence of a candidate compound relative to the measurable level of activity in the absence of the candidate compound. An increase in activity is witnessed if there is a gain by any amount such as, for example, by 2%, 5%, 10%, 15%, 25%, 35%, 45%, 55%, 65%, 75%, 85%, 95%, 100% or more, or, up to 1.5-fold, 2-fold, 5-fold, 10-fold, 20-fold, 50-fold, 100-fold or more in the presence of a candidate compound as compared to the absence of the candidate compound. Also, as used herein, the term "decrease" refers to a reduced level of measurable activity of a polypeptide in a given assay in the presence of a candidate compound relative to the measurable level of activity in the absence of a candidate compound. A "decrease" in activity is witnessed if there is at least 2%, 5%, 10%, 15%, 25%, 35%, 45%, 55%, 65%, 75%, 85%, 95% or less activity, for example, no activity, than that observed in the absence of a candidate compound.

As used herein, the term "antagonist" refers to a compound, the presence of which results in a decrease in the biological activity of Eya protein or a fragment of an Eya protein. In some embodiments, the term antagonist refers to a compound that results in a complete inhibition of the biological activity of Eya protein or a fragment of an Eya protein. In other embodiments, the term antagonist refers to a compound that partially inhibits the biological activity of Eya protein or a fragment of an Eya protein. A partial inhibition in the biological activity of Eya protein or a fragment of an Eya protein can include a decrease of 5%, 10%, 15%, 25%, 35%, 45%, 55%, 65%, 75%, 85%, or 95% or more, of a measured biological activity in the presence of an antagonist compound relative to its absence. Examples of biological activities of Eya polypeptides include, for example, binding of Eya to Six and the phosphatase activity of Eya and the like.

As used herein, the term "agonist" refers to a candidate compound, the presence of which results in an increase in the biological activity of Eya protein or a fragment of an Eya protein. In some embodiments, the term agonist refers to a candidate compound that is capable of inducing the biological activity of Eya protein of a fragment of an Eya protein. In some embodiments, the term agonist refers to a candidate compound that is capable of enhancing the biological activity of Eya protein of a fragment of an Eya protein. In other embodiments, the term agonist refers to a candidate compound that is capable of potentiating the biological activity of Eya protein of a fragment of an Eya protein. Examples of biological activities of Eya polypeptides include, for example, binding of Eya to Six and the phosphatase activity of Eya and the like. An increase in the biological activity of Eya protein or a fragment of an Eya protein can include an increase of 5%, 10%, 15%, 25%, 35%, 45%, 55%, 65%, 75%, 85%, or 95% or more, or 1.5-fold, 2-fold, 5-fold, 10-fold, 25-fold, 50-fold, 100-fold or more, of a measured biological activity in the presence of an agonist compound relative to its absence.

As used herine, the terms "candidate agent" or "candidate compound" or "candidate molecule" or "candidate drug" refers to an agent, compound, or molecule that can have a therapeutic effect, in some embodiments, in vivo. In other embodiments, the terms candidate agent or candidate compound or candidate molecule or candidate drug refers to an agent, compound, or molecule that has the potential to have a therapeutic effect in vitro. The term "candidate" is intended to convey the status of the agent, compound, molecule, or drug such that a therapeutic effect is not yet determined, but can exist. The candidate agent, compound, molecule, or drug can be selected from, for example, a compound or chemical library, a vendor, or any other source of small molecules (defined below) wherein the activity relative to the biological system of interest is unknown.

As used herein, "chemical library" or "compound library" refers to a collection of stored chemicals often used in high-throughput screening or industrial manufacture. The library can be a series of stored chemicals, each chemical typically having associated information stored in a database. The associated information can include, for example, the chemical structure, purity, quantity, and physiochemical characteristics of the compound. Chemical or compound libraries can focus on large groups of varied organic chemical series such that an organic chemist can make many variations on the same molecular scaffold or molecular backbone. Chemicals can also be purchased from outside vendors as well and included into an internal chemical library.

As used herein, the term "fragment" refers to a polypeptide having a sequence length ranging from 1 to n−1 with respect to the full length polypeptide of length n. The length of the fragment can be appropriately changed depending on the purpose. For example, the lower limit of the length of the fragment includes 3, 4, 5, 6, 8, 9, 10, 15, 20, 25, 30, 40, 50, 75, 100 or more amino acids. Lengths represented by integers that are not herein specified, for example, 11 and the like, can be appropriate as a lower limit Mutations, truncations, substitutions and other alterations of the sequence are included in the definition of fragment, provided some degree of the biochemical activity of interest is preserved.

As used herein, the term "disorder associated with Eya dysregulation" refers to a pathology or condition associated with abnormal levels of expression or activity of an Eya protein or gene, in excess of, or less than, levels of expression or activity in normal healthy mammals, where such excess or diminished levels occur, in some embodiments, in a particular cell type. In some embodiments, a disorder associated with Eya dysregulation refers to a pathology or condition associated with abnormal levels of expression or activity of an Eya protein or gene, in excess of, or less than, levels of expression or activity in normal healthy mammals, where such excess or diminished levels occur in a particular location in the body. In some embodiments, a disorder associated with Eya dysregulation refers to a pathology or condition associated with abnormal levels of expression or activity of an Eya protein or gene, in excess of, or less than, levels of expression or activity in normal healthy mammals, where such excess or diminished levels occur in a particular location in the body. In some embodiments, a disorder associated with Eya dysregulation refers to a pathology or condition associated with abnormal levels of expression or activity of an Eya protein or gene, in excess of, or less than, levels of expression or activity in normal healthy mammals, where such excess or diminished levels occur in a particular tissue in the body. In other embodiments, a disorder associated with Eya dysregulation refers to a pathology or condition associated with abnormal levels of expression or activity of an Eya protein or gene, in excess of, or less than, levels of expression or activity in normal healthy mammals, where such excess or diminished levels occur systemically. Such disorders include syndromes characterized by dysregulated cell growth such as cancer.

As used herein, the term "purified," in the context of a compound, for example, a compound identified in accordance with the method of the invention, refers to a compound that is substantially free of chemical precursors or other chemicals when chemically synthesized. In a specific embodiment, the compound is 60%, preferably 65%, 70%, 75%, 80%, 85%, 90%, or 99% free of other, different compounds.

As used herein, the terms "molecule" or "small molecule" refer to, for example, peptides, peptidomimetics, amino acids, amino acid analogs, polynucleotides, polynucleotide analogs, nucleotides, nucleotide analogs, organic or inorganic compounds (for example, heterorganic and/or organometallic compounds and the like) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The phrase "relevant biochemical activity" as used herein is intended to encompass that biochemical activity necessary for conducting the assay of interest, including, for example, the ability of the protein of interest to bind to or interact with another protein of interest, phosphatase activity, or DNA binding activity. For example, relevant biochemical activity with respect to Eya can include one or all of the following: transactivation activity, phosphatase activity, or binding with other proteins such as Six protein. With respect to Six protein or a fragment of a Six protein, relevant biochemical activity can include, for example, the ability to bind to or modulate Eya activity, or DNA binding.

A protein "variant" means a polypeptide having at some degree of sequence identity with the amino acid sequence of a native sequence full length protein wherein an identified biochemical activity of the variant is substantially preserved. Such variant polypeptides include, for instance, polypeptides wherein one or more amino acid residues are added, or deleted, at the N- and/or C-terminus, as well as within one or more internal domains, of the full-length amino acid sequence or fragment. Ordinarily, a variant polypeptide will have at least about 80% amino acid sequence identity, or at least about 81% amino acid sequence identity, or at least about 82% amino acid sequence identity, or at least about 83% amino acid sequence identity, or at least about 84% amino acid sequence identity, or at least about 85% amino acid sequence identity, or at least about 86% amino acid sequence identity, or at least about 87% amino acid sequence identity, or at least about 88% amino acid sequence identity, or at least about 89% amino acid sequence identity, or at least about 90% amino acid sequence identity, or at least about 91% amino acid sequence identity, or at least about 92% amino acid sequence identity, or at least about 93% amino acid sequence identity, or at least about 94% amino acid sequence identity, or at least about 95% amino acid sequence identity, or at least about 96% amino acid sequence identity, or at least about 97% amino acid sequence identity, or at least about 98% amino acid sequence identity and or at least about 99% amino acid sequence identity with a reference polypeptide or a specified fragment thereof. Variant polypeptides do not encompass the native polypeptide sequence.

As used herein, the term "treatment," with respect to disease, in some embodiments, refers to preventing the disease, for example, causing the clinical symptoms of the disease not to develop in an animal that is exposed to or predisposed to the disease, but does not yet experience or display symptoms of the disease. In some embodiments, the term treatment refers to inhibiting the disease, for example, arresting the development of the disease or its clinical symptoms. In some embodiments, the term treatment refers to relieving the disease, completely or partially, for example, causing regression of the disease or its clinical symptoms.

One skilled in the art will recognize many methods and materials similar or equivalent to those described herein that can be used in the practice of the present subject matter. Indeed, the present subject matter is in no way limited to the methods and materials described.

"ED" as used herein, refers to the Eya domain region, that region homologous to residues 238-510 of the murine Eya3 amino acid sequence, or an N-terminal deletion construct of human Eya1/2/3/4, homologous to the amino acid sequence of murine Eya including residues 179-510. See FIG. 2.

The instant invention relates to the novel finding that members of the retinal determination gene network (the "RDGN"), particularly the Six and Eya proteins, interact synergistically to increase phosphatase activity of the Eya protein. As such, this synergistic activity is useful for the development of more sensitive and accurate assays for the identification of novel therapeutics agents useful for the treatment of proliferative disorders such as cancer. Specifically, Six proteins have been discovered to interact with Eya to form a complex, wherein the Six protein modulates and increases tyrosine phosphatase activity of the Eya protein. This increase in tyrosine phosphatase activity is a useful parameter that can be measured for the purpose of identifying molecules that interact with this pathway. This novel finding underlies the basis for identification of therapeutic agents useful for the treatment or prevention of proliferative disorders such as various types of cancer.

The RDGN is a well conserved network that plays an important role in organ development and cell proliferation. First identified in drosophila, the RDGN encodes a set of nuclear transcription factors and/or cofactors including: twin-of eyeless (toy), eyeless/Pax6 (EY/Pax6), eye absent (EYA/eya), sine oculis (SO/Six), and dachshund (dac). In *Drosophila*, each of these genes is sufficient for eye determination and function together in a molecular network during development. The ectopic expression of each of these proteins results in ectopic eye formation in flies and lack of these proteins results in an eyeless phenotype.

Vertebrate homologs of eyeless (Pax6), sine oculis (Six 1-6), eyes absent (Eya 1-4), and dachshund (Dach 1-2) have been identified. Tissue specific vertebrate homologues of each of these proteins form part of analogous cascades implicated in the development of numerous organs including eye, muscle, kidney, ear, thymus, parathyroid and brain. The existing evidence suggests that key biochemical events marking early steps in cell fate determination are conserved across species and organ types. As discussed herein, members of the RDGN—such as Six and Eya—appear to be dysregulated in proliferative diseases such as cancer. As such, identification of novel mechanisms among these members provides novel targets for the treatment of such diseases.

Dachshund

The *Drosophila* dachshund (dac) gene is the founding member of the DACH subfamily of nuclear proteins. The DACH subfamily performs an important role in *Drosophila* in promoting differentiation of the eye and limb. Dachshund is a winged-helix class DNA-binding protein with transactivation and repression potential.

There are two mammalian Dach genes, Dach1 and Dach2. Interaction between Dach and Six6 has been observed in mammalian two-hybrid and GST-pulldown experiments. However, the degree of specificity and the domains involved in Six6-Dach interaction are not known.

Eyeless/Pax6 (EY/Pax6)

Drosophila eyeless (ey) derives its name from the 'eyeless' phenotype that is caused by eye-specific, loss-of-function alleles of the ey gene. The cloning of ey revealed its homology to the vertebrate Pax6 transcription factors, which encode a subgroup of the large family of PAX proteins. The PAX proteins each contain two DNA-binding motifs: a PAIRED box, and a HOMEOBOX. The Pax6 family members act as 'master regulators' of eye formation, and function at the top of a transcriptional hierarchy, in that they are generally required for downstream members of the RDGN, though this hierarchy is not absolute. Eya, sine oculis (so) and dac are downstream components of this network. (Silver, et al., Development, 2005.)

SIX Family Members

Six family genes have been identified in human, mouse, fly, chicken, frog, and nematodes, but not in unicellular organisms such as yeast. In flies, there are three Six family genes (so, optix, and D-Six4). In mammals there are six Six genes (Six 1-6). Six proteins can be categorized into three subfamilies based on molecular phylogenetic analysis of their amino acid sequences. These are Six 1/2 (Drosophila sine oculis homologues), Six 3/6 (Drosophila optix homologues) and Six 4/5 (Drosophila D-Six 4 homologues.)

Mammalian Six proteins vary in length between 277 and 776 residues, having two regions of high sequence conservation: a 59-residue homeodomain ("HD") and a 115-123 residue "Six" domain ("SD") which is N-terminal to the HD. The Six HD belongs to the K50 class in which the key DNA interaction residue—arginine at position 50—is replaced by a lysine. The Six domain is highly conserved among the Six proteins (43% identity) and bears no resemblance at the primary structural level to proteins/domains with known structure or function. N- and C-terminal to the Six homeodomains are regions of low conservation in terms of both length and sequence. In vivo data suggests that the C-terminal region of Sine oculis is important for its role in eye development. There is also evidence that Six1 is phosphorylated C-terminal to the HD. The Six4/5 proteins contain a transactivation domain at the extreme C-terminus.

The biological functions of the various Six proteins have been largely inferred from phenotypic analyses of Six family mutants and from over-expression studies. Six genes are widely expressed during vertebrate embryogenesis, suggesting that they are implicated in diverse differentiation processes, and have roles other than in retinal determination. Although definitive loss-of function data are not yet available for all members of the Six family, some biological roles are reasonably well-established. In Drosophila, for example, Sine oculis is involved in the development of the entire visual system. In addition, the embryonic lethality of some Sine oculis mutants suggests that it plays an important role in the development of other tissues.

The vertebrate Sine oculis homologue Six1 appears to have different functions. Mice lacking Six1 die at birth due to thoracic skeletal defects and severe muscle hypoplasia affecting most of the body's muscles. Six1−/− neonates lack a kidney and thymus, and have disorganized craniofacial structures such as the inner ear, nasal cavity, craniofacial skeleton, and the lacrimal and parotid glands. Six1 and Six4, which have partially overlapping expression patterns, seem to have distinct biological roles. Unlike the Six1−/− mice, Six4−/− mice have few defects in embryogenesis or skeletal muscle development. Thus, while Six1 can compensate for the lack of Six5, Six4 does not compensate for the lack of Six1.

Over-expression studies in zebrafish, medaka, Xenopus, and chicken suggest that the vertebrate Six3/6 genes are involved in forebrain and eye development. Six −/− mice exhibit a hypoplastic pituitary gland and varying levels of retinal hypoplasia. An interesting generalization that seems to be emerging is that the Six proteins are able to stimulate proliferation of committed cells before they terminally differentiate. This function is particularly relevant as overexpression of Six genes has been reported in several tumors. See, for example, Table 1.

The regulatory targets of some Six proteins are known, and Six DNA binding sites have been identified using DNA footprinting and related techniques. Six4, Six2 and Six5 bind to the "ARE" regulatory element of the Na+/K+ ATPase α1 subunit gene, GGTGTCAGGTTGC (SEQ ID NO. 1), with a consensus minimum binding sequence of GGnGnCnGGT-TGC (SEQ ID NO. 2). The closely related MEF3 motif, TCAGGTT (SEQ ID NO. 3) (underlined in the ARE motif), present in the myogenin promoter is also recognized by Six 1 and Six 4. However, a recent analysis suggests that Six4's DNA sequence preferences are more stringent than those of Six1. Rayapureddi and Hegde (2006) FEBS Let. 580(16): 3853-3859. Six 4 can also bind to a site in the muscle creatine kinase enhancer (the Trex site) that is related in sequence to the MEF3 site The consensus Trex/MEF3 sequence is TC[G/A]GGT[G/T] (SEQ ID NO. 4). Interestingly, published reports suggest that Six3 does not bind to either the ARE or the MEF3 sites. In PCR-based selection experiments Six3 binds to the classical homeodomain core tetranucleotide ATTA. Using the chemical nuclease 1,10-phenanthroline-Cu covalently linked to the protein, Hazbun et al have identified [C/T].GATAC (SEQ ID NO. 5) as a binding sequence for the sine oculis HD. This sequence bears no resemblance to the ARE, MEF3 or Trex sites identified as Six1/2/4 binding sequences. It is possible that the Six proteins also bind to the sine oculis sequence and vice-versa.

Several Six protein-protein interactions have been reported implicating the Six proteins in diverse biochemical functions, though no recognizable sequence or structural signatures are shared among the Six binding proteins. Further, little is known about the effect of each interaction on Six function. Yet their biological importance is underscored by the fact that mutations associated with disease states are known to disrupt some interactions and animal models predict severe phenotypes when other interactions are disrupted.

There have been several reports associating various Six proteins with cancer. Six1 is over-expressed in breast cancer cells and is highest in metastatic lesions. It is a cell cycle regulated gene and also plays a role in tumorigenesis and tumor progression. Ford, et al. (2000) J. Biol. Chem. 275(29): 22245-22254; Ford et al., (1998) Proc. Nat'l Acad. Sci USA 95(21): 12608-12613. There is no detectable Six1 mRNA in normal mammary epithelium while 44% of primary tumors and 90% of metastatic lesions show more than a 3-fold increase of SIX 1 mRNA relative to adjacent normal breast tissue. Six1 overexpression is thought to reinstate an embryonic pathway of proliferation in breast cancer by up-regulating cyclin A1. Ford et al., (1998) Proc. Nat'l Acad. Sci USA 95 (21): 12608-12613; Coletta et al. (2004) Proc. Nat'l Acad. Sci USA 101(17): 6478-6483. Six1 up-regulation is also seen in metastatic rhabdomyosarcomas, the most common pediatric, soft-tissue sarcoma, correlating with clinical stage. Yu et al. (2004) Nat. Med. 10(2): 175-181; Laflamme et al. (2003) Can. Res. 63(2): 449-454. Six4 has been identified as a breast cancer candidate gene; it is mutated in 11% of the breast cancer samples studied. Sjoblom et al. (2006) Science 314 (5797): 268-274. There is also a suggestion that Six3 deregulation is associated with human extra-skeletal myxoid chondrosarcoma (EMC) tumors, by disrupting the balance between the expression of the orphan nuclear receptor NOR-1 and the EWS/NOR-1 fusion protein. Human Six1 is overexpressed in breast cancer cells and is highest in metastatic lesions. It is a cell cycle regulated gene and also plays a role in tumorigenesis and tumor progression. Six1 upregulation is also seen in metastatic rhabdomyosarcomas, the most common pediatric soft-tissue sarcoma, correlating with clinical stage. There is also a suggesting that Six3 deregulation is associated with human extra-skeletal myxoid chondrosarcoma (EMC) tumors, by disrupting the balance between the expression of the orphan nuclear receptor NOR-1 and the EWS/NOR-1 fusion protein. In fact, Six4 has been identified as a breast cancer candidate gene, mutated in 11% of the breast cancer samples studied. As such, Six dysregulation is associated with a variety of disease states, including proliferative disorders such as cancer.

The accession numbers for human SIX proteins 1-6 are as follows: *Homo sapiens* sine oculis homeobox homolog 1 (*Drosophila*) (Six1), mRNA, Accession number NM_005982.2; *Homo sapiens* sine oculis homeobox homolog 2 (*Drosophila*) (Six2), mRNA, Accession number NM_016932.3; *Homo sapiens* sine oculis homeobox homolog 3 (*Drosophila*) (Six3), mRNA, Accession number NM_005413.2; *Homo sapiens* sine oculis homeobox homolog 4 (*Drosophila*) (Six4), mRNA, Accession number NM_017420.3; *Homo sapiens* sine oculis homeobox homolog 5 (*Drosophila*) (Six5), mRNA, Accession number NM_175875.3; *Homo sapiens* sine oculis homeobox homolog 6 (*Drosophila*) (Six6), mRNA, Accession number NM_007374.1. Sequences of corresponding Six proteins in other species are known and/or are readily ascertainable by one of ordinary skill in the art using standard molecular biology methods.

In the context of the instant disclosure, full length Six proteins are generally used, though it would be readily understood to one of ordinary skill in the art that the regions of the protein responsible for the biochemical properties necessary to carry out the methods of the disclosure can be readily determined such that fragments or partial sequences can also be within the scope of the invention.

Eyes Absent (Eya)

Eyes Absent proteins (Eya), belonging to the haloacid dehalogenase class of enzymes, share a sequence signature consisting of three conserved motifs with the haloacid dehalogenase (HAD) family of enzymes. Studies of *Drosophila* Eya and of its vertebrate homologs Eya 1-4 have revealed important roles for these genes in cell survival and differentiation, particularly during tissue specification.

Figure 2:
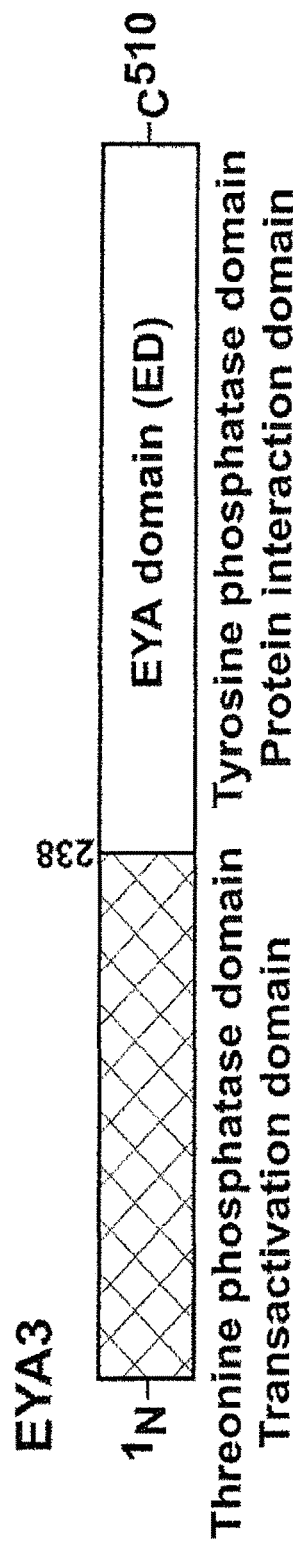
FIG. 2 is a representation of the domain architecture of Eya. The EYA domain (ED) is the tyrosine phosphatase domain.

Eya is a cofactor of Six proteins (described below) and contains the conserved Eya domain indispensable for Tyrosine phosphatase and SIX interaction activity. FIG. 2. The Eya proteins are involved in cell-fate determination in both vertebrates and invertebrates. Eya proteins range in size from 510 to 760 amino acids containing a highly conserved 271-274 residue C-terminal domain, the "Eya domain" or "ED," which participates in protein-protein interactions. Human homologues, Eya 1-4, are strikingly similar in their Eya domain. The N-terminal domains are crucial for the transcriptional co-activator function of Eya. The Eya protein, however, has no known direct DNA-binding activity.

The Eya proteins were thought to be transactivators, until it was shown that these proteins—in the C-terminal region—also have tyrosine phosphatase activity. Thus Eya is a unique molecule with dual biochemical functions. Bonini et al. (1993) *Cell* 72(3): 379-395; Bonini et al. (1997) *Development* 124(23):4819-4826; Rayapureddi et al. (2003) *Nature* 426 (6964):295-298; Tootle et al. (2003) *Nature* 426(6964):299-302. The Eya proteins are both nuclear transcription factors (acting through interaction with homeodomain-containing Six proteins) and protein tyrosine phosphatases (PTPs). A schematic representation of the domain structure of EYA3 is shown in FIG. 2.

Of particular significance is the fact that Eya proteins are different from other tyrosine phosphatases in the mechanism of action. That is, the Eya proteins, unlike other PTPs that use cysteine as a nucleophile (a thiol-based mechanism), use an aspartate residue in a metal-dependent reaction. This unique, non-thiol based mechanism is described in Rayapureddi et al (2005) *Biochemistry*; Rayapureddi et al. (2003) *Nature* 2003; incorporated herein by reference.

As such, the Eya protein and modulation of Eya phosphatase activity is a valuable drug discovery target. While PTPs in general are emerging as important new targets for cancer therapy, PTPs as a target have limitations that confound the practical utility of this approach. (reviewed in Easty et al. (2006) *Curr. Cancer Drug Targets* 6(6):519-532). Because PTPs share a common, thiol-based mechanism, the design of PTP inhibitors has been hampered by the inability to achieve specificity among the large family of mammalian PTPs. Due to the conserved regions of the active site, particularly the conserved cysteine residue, among PTPs, targeting specific PTPs has proved difficult.

Agents that specifically target PTPs have enormous potential in the treatment of proliferative disorders such as cancer. Though approximately 30% of cellular proteins are phosphoproteins, tyrosine phosphorylation accounts for only about 0.01% to about 0.05% of all phospho-proteins. In disease states such as oncogenic transformation, however, tyrosine phosphorylation is increased up to one to two hundred-fold to 1 to 2% of the total phospho-protein population. While protein tyrosine phosphatases have been extensively linked with disease states including proliferative diseases such as cancer (See Table 1), the design of tyrosine phosphatase inhibitors, as discussed above, has traditionally been confounded by a lack of specificity.

In contrast to most PTPs, the Eya family of PTPs forms a distinct structural class that act by a distinct mechanism, providing a unique opportunity for identification of novel molecules to treat or prevent proliferative disorders. Because the Eya family of protein tyrosine phosphatases uses an aspartate residue as a nucleophile instead of the thiol-based mechanism used by classical PTPs, the Eya proteins represent an attractive new target for novel pharmacological therapies for proliferative diseases, wherein a unique mechanism of action allows a means to specifically target these tyrosine phosphatases. The discovery that Eya phosphatase activity is regulated via Six protein, in combination with the methods disclosed herein, provide a novel target and method for identification of molecules that can be used for the treatment of proliferative disorders that are likely to provide sufficient specificity for practical utility.

Dysregulation of Tyrosine Phosphorylation in Disease States

Tyrosine phosphatase activity is upregulated in many disease states. Examples of PTPs and associated diseases are listed in Tables 1 and 2. Traditional PTPs operate via a thiol-based mechanism, using a cysteine as a nucleophile. In contrast, Eya, operates using a non-thiol based mechanism in which an aspartate residue is the nucleophile. As such, Eya represents a molecule that can be specifically targeted.

TABLE 1

PTPs and Disease

| Protein Tyrosine Phosphatase | Disease/Disorder |
| --- | --- |
| PTP1B | Diabetes and Obesity |
| CD45 | Autoimmunity |
| SHP1 | Inflammation |
| YopH | Infectious Diseases |
| MTM1 | X-Linked myotubular myopathy |
| VH1 | Infectious Diseases |

TABLE 2

PTPs implicated in Cancer

| Protein Tyrosine Phosphatase | Role in Cancer |
| --- | --- |
| PTEN | Tumor Suppressor mutated in various cancers |
| DEP1 | Tumor suppressor, primary CNS lymphomas |
| SHP2 | Noonan syndrome, stomach ulcers |
| Cdc25 | Over-expressed in primary breast cancers |
| PRL-3 | Metastasis, colon cancer |
| FAP-1 | Up-regulated in cancers |

Thus, Eya proteins and activity is a promising target for the treatment of many disorders including proliferative disorders such as cancer. Eya4 has been shown to be upregulated in malignant nerve cell sheath tumors. Miller et al (2009) *Oncogene* [epub November 9] Eya2 has been suggested to be a colon cancer candidate gene and is up-regulated in epithelium ovarian cancer. Similarly, Eya2 expression is upregulated in breast cancer. Eya2 overexpression is also associated with increased tumor size in mouse models, while Eya3 overexpression results in increased cell proliferation in vitro. The association between Eya expression and cancers is only just emerging. In analyses of several cancer gene expression databases Eya3 is over-expressed in samples from breast cancer patients as well as in breast cancer cell-lines, often correlating with increased malignancy. High levels of Eya2 mRNA was found in 4 (SKBR75, MCF-7, MDA-MB-468, and 2R75-1) of 5 breast cancer cell lines tested by RT-PCR. Zhang et al. (2005) *Cancer Res.* 65(3):925-932. Analysis of microarray data archived at the Gene Expression Omnibus repository at the National Center for Biotechnological Information also reveals over four-fold over-expression of Eya2 in the cell line HCC 1954 derived from a grade III invasive ductal breast carcinoma cancer cell line, relative to the non-invasive cell line MDA-MB-436. Eya2 is also up-regulated in epithelial ovarian tumors and promotes tumor growth. Zhang et al. (2005) *Cancer Res.* 65(3):925-932. As such, Eya itself represents a promising target for development of novel therapeutic agents for the treatment and prevention of proliferative disorders. The methods disclosed herein provide a means of identifying such agents.

In addition to Eya protein expression, the level of tyrosine phosphorylation is reportedly higher in cancer tissue relative to normal epithelium, commensurate with higher protein tyrosine kinase (PTK) levels. Hennipman et al. (1989) *Cancer Res.* 49(3): 516-521; See Tables 1 and 2.) This is in keeping with the conventional wisdom that PTKs support transformation and cell proliferation. Since PTPs have typically been classified as tumor suppressors, the observation that protein tyrosine phosphatase activity is also increased in cancer tissue can seem counterintuitive. However many of the protein tyrosine phosphatases (PTP) over-expressed in cancer (such as, for example, PTPa, PTP1B, PTPeM) have been shown to dephosphorylate and activate the oncogenic PTK c-src which accounts for 70% of the elevated PTK activity in breast cancer. Ottenhoff-Kalff et al. (1995) *Breast Cancer Res. Treat.* 33(3): 245-256.

The Eyes Absent domain (ED) (238-510 in mouse EYA3) is thought to be involved in Six interaction. In fact, the ED domain has tyrosine phosphatase activity and contains the three motifs characteristic of the haloacid dehalogenase class of enzymes. Eyes Absent proteins contain a sequence signature made up of three conserved motifs. The first is an N-terminal hhhhDxDxT/s. Motif II is a central hhhT Motif III is a C-terminal Kx(n) hhhhGDxxxD/E. "h" refers to hydrophobic residues, while "x" refers to any amino acid. (Rayapureddi, J. et al, (2005) *Biochemistry*.)

The accession numbers of homologues of the Eya sequence in homo sapiens are as follows: *Homo sapiens* eyes absent homolog 1 (*Drosophila*) (Eya 1), transcript variant 1, mRNA, Accession number NM_172060.1; *Homo sapiens* eyes absent homolog 2 (*Drosophila*) (EYA2), transcript variant 1, mRNA, Accession number NM_005244.3; *Homo sapiens* eyes absent homolog 3 (*Drosophila*) (EYA3), mRNA, Accession number NM_001990.2; *Homo sapiens* eyes absent homolog 4 (*Drosophila*) (EYA4), transcript variant 1, mRNA, Accession number NM_004100.3.

Novel Mechanism of Action: Synergism between SIX and Eyes Absent

The methods disclosed herein relate to the novel finding that Six and Eya proteins interact and synergize, resulting in increased Eya tyrosine phosphatase activity. This, in turn, is expected to result in increased cell proliferation, growth, and migration that occur in pathological states such as cancer or other proliferative disorders. This newly-discovered synergistic DNA-binding and tyrosine phosphatase activities of the Six-Eya complex exemplify a novel molecular mechanism that is a promising target for identifying therapeutic agents for the treatment and prevention of various diseases including, for example, proliferative disorders such as cancer.

Interaction between Six proteins and the Eya class of transcription factors/phosphatases was originally reported for the *Drosophila* proteins sine oculis and eyes absent. Subsequently, interaction between mammalian Six and Eya proteins was reported. The biological relevance of the Six-Eya interaction is evidenced by the fact that amino acid substitutions in Eya proteins that disrupt this interaction are associated with branchio-oto-renal syndrome, a multi-organ developmental disorder.

A schematic of the prevailing view of the Six-Eya protein interaction is shown in FIG. 1. As described above, the Six proteins are homeodomain containing transcription factors that can act as activators or repressors of transcription based on their cellular partners. The Eya proteins are both transactivators and tyrosine phosphatases. The current view holds that the interaction of Six with Eya is a tethering mechanism that anchors Eya to DNA such that it can carry out its transactivation function.

For the first time, it is now shown that the DNA binding affinity of the Six protein transcription factors and the phosphatase activity of the Eya proteins are actually increased upon complex formation, suggesting the novel synergistic mechanism shown in FIG. 1. It has recently been found that Six and Eya proteins interact and synergize to induce cell proliferation and migration. As such, there appears to be a connection between synergistic regulation of Six and Eya and proliferative potential. This novel mechanism provides a new target for identification of pharmacological agents. Agents that are able to modulate this interaction, and downstream effects of this interaction, have the potential to be useful, for example, in attenuating cellular proliferation and treating or preventing disorders related to cellular proliferation such as cancer.

Interaction between Six and Eya protein, for example, Six1 and Eya2 which are overexpressed in proliferative disorders such as breast cancer, results in a significant increase in the catalytic activity of the Eya proteins and a dramatic enhancement of Six-DNA binding affinity.

This synergistic interaction of Eya and Six protein is exemplified in the data shown in FIG. 6. FIG. 6a shows that addition of a Six2 fragment of the to Eya3 results in a significant increase in Eya 3 phosphatase activity towards a peptide derived from its physiological substrate H2AX. These results are compared to Eya3 alone, without the presence of Six2. FIG. 6b shows that the phosphatase activity of Eya3 is further increased when it interacts with a complex of SIX2 and a DNA fragment containing a SIX2 binding site. FIG. 6c shows that the interaction with Eya3 increases the DNA binding affinity of SIX2. These synergistic DNA-binding and tyrosine phosphatase activities of the Six-Eya complex represent a novel molecular mechanism and target useful for the identification of novel therapeutic agents. The data shown in FIG. 6 employ a Six2 fragment derived from mouse Six protein having the following amino acid sequence: MSMLPTFGFTQEQVACVCEVLQQGGNI-ERLGRFLWSLPACEHLHKNESVLKAKAVVAF HRGN-FRELYKILESHQFSPHNHAKLQQLWL-KAHYIEAEKLRGRPLGAVGKYRVRRKFP LPRSIWDGEETSYCFKEKSRSVLREW-YAHNPYPSPREKRELAEATGLTTTQVSNWFKNR RQRDRAAEAKERENSENSNSSSH-NPLASSLNGSGKSVLGSSEDEKTPSGTPDHSSSSPAL LLSPPPPPGLPSLHSLGHPPGP-SAVPVPVPGGGGADPLQHHHSLQDSIL-NPMSANLVDLG S (SEQ ID NO. 6). Full-length murine Eya3 is used in the experiments used to generate the data in FIG. 6.

The finding that Eya and Six interact synergistically now adds several degrees of complexity to the existing model of the Eya-Six interaction. That is, the interaction is not merely a tethering of Eya to DNA by Six to carry out its transactivation function as previously thought. Rather, this interaction causes a mutual modulation of the biochemical activities of both the Six and Eya proteins. Given the synergistic effects and increased phosphatase activity of this complex, the Eya-Six interaction can be used as a robust screening tool for the discovery of novel compounds for the treatment of proliferative disorders, using the methods disclosed herein.

Additional controls can be included, that can be, for example, a cell that is the same type of cell as that of test cells except that the control cell is not exposed to a candidate agent. An appropriate control can be run simultaneously, or it can be pre-established, for example, a pre-established standard or reference.

Eya fragments that can be used are those that contain Eya3 residues 179-510 which has been previously reported to be the minimum construct necessary for Six2 interaction Ohto et al., (1999) *Mol Cell Biol* 19: 6815-6824. Cooperation of six and eya in activation of their target genes through nuclear translocation of Eya, or Eya3 residues 238-510 which contain the conserved Eya domain (ED) that houses the phosphatase activity. Rayapureddi et al. (2003) *Nature* 426:295-298. Eyes absent represents a class of protein tyrosine phosphatases.

High throughput assays can be used for identification of potential therapeutic agents. Such methods are readily understood by one of ordinary skill in the art. In general, such methods as applied to the instant disclosure include providing Eya and Six proteins or fragments, for example, full length Eya3 and full length Six protein and a test compound, using pNPP, pY, phosphorylated peptides or phosphorylated proteins as a substrate under conditions optimal for catalytic activities in the presence of stochiometric amounts of the Six and Eya protein. Phosphatase activity can then be qualitatively or quantitatively determined, wherein those test compounds that decrease or inhibit phosphatase activity are considered lead compounds suitable for further investigation.

Drug Discovery and Drug Lead Optimization

The methods and compositions disclosed herein are useful in drug discovery and drug lead optimization processes. As part of compound screening efforts, the use of the targets described herein can be used to identify compounds or molecules that can be useful as novel therapeutic agents for the treatment of cancer or other proliferative disorders associated with dysregulated Eya phosphatase activity. As such, the instant disclosure also encompasses methods of screening molecules to identify those that can act as agonists or antagonists of the Six/Eya interaction.

Such molecules can be small molecules or polypeptides, including antibodies. For example, antibodies that specifically target either the Six-Eya complex or the Six or Eya proteins by themselves and that inhibits or otherwise modulates Six and Eya interaction and/or the activity of either protein can also be employed in the presently disclosed methods. Monoclonal antibodies can be prepared using hybridoma methods, such as those described by Kohler and Milstein (1975) *Nature* 256: 495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro. The immunizing agent will typically include a Six or Eya polypeptide or a fusion protein thereof. The immunizing agent can alternatively include a fragment or portion of Six or Eya having one or more amino acids that participate in the binding of Six to Eya. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) (pp. 59-103) Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Examples of small molecules include, but are not limited to, small peptides or peptide-like molecules, preferably soluble peptides, and synthetic non-peptidyl organic or inorganic compounds. The screening assays for drug candidates are designed to identify compounds or molecules that bind or complex with the ligand or receptor polypeptides identified herein, or otherwise interfere with the interaction of these polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art. Assays for instance, antagonists are common in that they call for contacting the drug candidate with a ligand or receptor polypeptide identified herein under conditions and for a time sufficient to allow these two components to interact.

Small molecules identified using the methods described herein can be modified based on analysis of molecule-target interactions using modeling techniques as known in the art, giving rise to optimized, and sometimes unique, chemical structures. Mutational analysis of both Six and Eya proteins can be used to identify amino acid residues involved in the interaction between molecule and target. Knowledge of such residues permits the development of compounds with the correct positioning of functional groups that will optimally interact with the key residues in the target. The ability to identify key functional residues will provide utility in efforts to design chemical molecules that are selective for the specific target while having limited or no interaction with other proteins. Since inadequate selectivity and reduced disease target specificity and 'side effects' frequently limit the utility of drugs, this aspect of the utility of the invention will be extremely valuable. These "hits" can be based on unique chemical structural 'platforms' that can be modified through medicinal chemistry. The hits are then subjected to lead optimization, which is used to identify related therapeutic agents that can possess improved properties, for example, activity, side effects, or drug-likeness.

In general, lead optimization, as known in the art, consists of the following general steps, which can be applied to the compounds and methods disclosed herein:

From identification of a "hit," a compound that is found to be active (i.e., exert a desired biochemical effect) in the initial screen, compounds are selected based on determination of $IC_{50}$, $EC_{50}$, or $AC_{50}$ values. Hits are confirmed, as described above, either using the same or a different assay, particularly that of a functional assay or in a cellular environment. A second or third screen can be used to provide additional validation of function. Hits can then be evaluated according to their synthesis feasibility and other parameters such as up-scaling or costs. If the target is known, biophysical testing, such as nuclear magnetic resonance (NMR), isothermal titration calorimetry, dynamic light scattering, or surface plasmon resonance can be used to assess whether the compound binds effectively to the target, or to identify stoichiometry of the binding or the presence of promiscuous inhibitors. Confirmed hit compounds, such as those described in Table 3, can then be ranked according to the various hit confirmation experiments.

After confirmation of the initial hits, compounds can be clustered according to characteristics in the previously defined tests and/or overall similarity to the hit. In identifying a compound cluster, characteristics such as affinity towards the target (preferably less that 1 µM), chemical tractability, binding to the P450 enzymes, P-glycoproteins or serum albumin (wherein a lack of interference with these proteins are preferred), solubility in water, stability, membrane permeability, druglikeness, lack of cytotoxicity, metabolism (rapidly metabolized compounds are not preferred), and selectivity with an identified target. Compounds having preferred or optimal pharmacokinetic properties, ease of manufacture, solubility, safety, toxicity, metabolism, synthesis feasibility and other parameters such as up-scaling or costs, etc. can be determined.

For example, from the list of compounds provided herein, one of ordinary skill in the art can apply standard methods and principles of medicinal chemistry to arrive at optimized compound structures that are preferred for administration to a mammal.

This can be done using a variety of different commercially available software packages or services which specialize in drug discovery, including lead discovery and optimization. See for example, Pharmacopeia Business Development, Princeton, N.J., which provides drug lead optimization services.

Structure-activity analysis can be conducted to identify core structures necessary for biological activity, such that additional compounds, derived from the initial hits shown in Table 3 or related compounds shown in Table 4, can be identified. Quantitative structure-activity relationship (QSAR) is the process by which chemical structure is quantitatively correlated with a well defined process, such as biological activity or chemical reactivity. For example, biological activity can be expressed quantitatively as in the concentration of a substance generally required to give a certain biological response. Additionally, when physiochemical properties or structures are expressed by numbers, one can form a mathematical relationship, or quantitative structure-activity relationship, between the two. The mathematical expression can then be used to predict the biological response of other chemical structures. The basic assumption for all molecule based hypotheses is that similar molecules have similar activities. This principle is also called Structure-Activity Relationship (SAR). It is well known for instance that within a particular family of chemical compounds, especially of organic chemistry, that there are strong correlations between structure and observed properties.

QSAR's most general mathematical form is:

Activity=$f$(physiochemical properties and/or structural properties)

3D-QSAR refers to the application of force field calculations requiring three-dimensional structures, e.g. based on protein crystallography or molecule superposition. It uses computed potentials, e.g. the Lennard-Jones potential, rather than experimental constants and is concerned with the overall molecule rather than a single substituent. It examines the steric fields (shape of the molecule) and the electrostatic fields based on the applied energy function. The created data space is then usually reduced by a following feature extraction (see also dimensionality reduction). The following learning method can be any of the already mentioned machine learning methods, for example, support vector machines. The partial least squares (PLS) method can also be used, in which the feature extraction and induction 3D-QSAR, referring to the application of force field calculations requiring three-dimensional structures, e.g. based on protein crystallography or molecule superposition, can also be used to predict preferred compounds. This method uses computed potentials, for example, the Lennard-Jones potential, rather than experimental constants and evaluates the overall molecule rather than a single substituent. In this method, the steric fields (shape of the molecule) and the electrostatic fields based on the applied energy function are examined and optimized. See, for example, A. Leach, *Molecular Modeling: Principles and Applications*, Prentice Hall, 2001; Schölkopf, B., K. Tsuda and J. P. Vert: *Kernel Methods in Computational Biology*, MIT Press, Cambridge, Mass., 2004; C. Helma (ed.), *Predictive Toxicology*, CRC, 2005; all incorporated herein in their entirety by reference. The created data space is then usually reduced by a following feature extraction (see also dimensionality reduction).

After compounds are selected based on the likelihood of the compound to exhibit similar bioactivity, such compounds can be further selected on the basis of drug-likeness. While the compounds of the UC/GRI library are enriched for compounds having drug-like properties, the following analysis is applicable in identifying preferred compounds or in screening libraries which are not enriched for such compounds.

"Drug-likeness" refers to how druglike a substance is. This can be estimated from the molecular structure before the substance is synthesized and tested. A druglike molecule has properties such as optimal solubility to both water and fat, because an orally administered drug passes through the intestinal lining, be carried in aqueous blood, and penetrate the lipid cellular membrane to reach the insider of a cell. The model compound for the cellular membrane is octanol, so the logarithm of the octanol/water partition coefficient, known as log POW is used to estimate solubility. The compound can also be selected on the basis of overall water solubility, as therapeutic agents typically are carried in aqueous media such as blood and intracellular fluid. Solubility in water can be estimated from the number of hydrogen bond donors versus alkyl sidechains in the molecule. Low water solubility translates to slow absorption and action. Too many hydrogen bond donors, on the other hand, lead to low fat solubility, so that the drug generally does not penetrate the cell wall reach the inside of the cell. Druglike substances are also those that are relatively small in molecular weight, as this parameter determines diffusion. Compounds less than about 1000 Daltons, or about 800 daltons, or about 500 daltons, or about 450 daltons can be used. 80% of traded drugs have molecular weights under 450 daltons. Druglikeness is also determined based on the presence of substructures that have known pharmacological properties.

As a means of predicting general druglikeness, "Lipinski's Rule of Five" can be used. This rule allows one to generally determine if a chemical compound with pharmacological or biological activity has properties that make it a likely orally active drug in humans. This rule is based on the general observation that most therapeutic agents are relatively small and lipophilic molecules. The rule describes molecular properties important for a drug's pharmacokinetics in the human body, including absorption, distribution, metabolism and excretion ("ADME"). In addition to evaluating identified compound clusters, this rule can be used to modify or optimize a lead structure step-wise for increased drug-like properties. For example, these principles can be applied to modify the molecular structure of a compound in the compound cluster or modification of a hit or lead compound to arrive at compounds having ideal molecular weights, rings, bonds, or lipophilicity.

Lipinski's Rule of Five (all numbers in the rule are multipliers of the number 5) states that, in general, an orally active drug has: 1) not more than 5 hydrogen bond donors (OH and NH groups), 2) not more than 10 hydrogen bond acceptors (notably N and O); 3) a molecular weight under 500 g/mol; 4) a partition coefficient log P less than 5. Lipinski et al. (2001) Adv. Drug Del. Rev. 46, 3-26, incorporated herein by reference. Software for calculating properties and predicting bioactivity of a compound is readily available, for example, at www.molinspiration.com.

The compounds can be further optimized according to guidelines set forth in Ghose, et al. (1999) J. Comb. Chem. 1: 55-68. These are: partition coefficient log P in −0.4 to +5.6 range; molar refractivity from 40 to 130; molecular weight from 160 to 480; number of heavy atoms from 20 to 70.

In addition to application of the Rule of Five, preferred compounds can be selected based on the predicted ADME. ADME refers to absorption, distribution, metabolism or excretion; compounds can be selected as preferred compounds for additional screening or testing for efficacy as a therapeutic compound on this basis. QSPR or QSAR can be used to predict the ADME and toxicity of a compound.

Based on an assessment of this information, druglikeness indexes can be constructed based on molecular fragments of structures (Xu and Stevenson 2000). The "drug like index" (DLI) is can be constructed according to a formula that uses the true and false positives, or true and false negatives in any set of best results that were obtained using the types of data described above. The DLI can be used for prioritizing molecules in any set of given structures, such as within the data sets of molecules obtained via High Throughput Screening (HTS) for molecular hits, in preparing lists of combinatorial chemistry for synthesis, or in assigning structures for High Throughput in Silico Docking of molecules, or those compound clusters described herein. The DLI can be further used for optimization of identified compounds (such as those listed herein) toward viable pharmaceutical agents by combinatorial addition of substituents that optimize their drug likeness. Using computational docking experiments as known in the art, DLI can also be combined with scores for the affinity. DLI can be used to decide how to reduce compound sets so that smaller sets can be examined (by HTS) or synthesized (by Combinatorial Chemistry). In summary, the DLI allows stratification of compounds such one can readily select compounds likely to be useful as therapeutic agents in practice. After selection of these compounds, routine testing of these compounds, including in vitro and in vivo testing, can be carried out.

In accordance with the above-described methods, US 2007/0156343, Rayan et al., filed Oct. 24, 2004, is incorporated in its entirety by reference.

While specific embodiments of the subject invention have been discussed, the above specification is illustrative and not restrictive. Many variations of the invention will become apparent to those skilled in the art upon review.

Assays

The following assays and protocols are employed in carrying out the above-described methods. Variations to these methods will be understood by one of ordinary skill in the art, and such variations are not intended to be excluded from the scope of the invention.

Phosphatase Activity Assay. Phosphatase activity of Eya is measured using the p-nitrophenyl phosphate (pNPP) assay. In this assay, reaction mixtures of approximately 60 uL in 20 mM MES (pH 5.5), various concentrations of pNPP and cations are pre-equilibrated at 30° C. for 10 minutes. The assay is initiated by the addition of 0.3 ug of enzyme in 20 mM Tris (pH 8.0) and 150 mM NaCl. The reaction mixture is incubated for 20 minutes, and then quenched with 100 uL of 0.4 M EDTA, pH 10.0. Release of p-nitrophenol (pNP) is monitored by measuring absorbance at a wavelength of 410 (A410) and extrapolating the values into the Michaelis-Menten equation using SIGMAPLOT (SPSS Science, Chicago, Ill.). pNP release can be plotted as a function of time when various enzyme concentrations are used.

Phosphatase activity can also be measured wherein reaction mixtures of approximately 60 uL with different concentrations of substrate (40-1500 uM phosphopeptides, 0.1-5 mM phosphoamino acids, or dNTPs), 20 mM MES, pH 5.5, and 2 mM $MgCl_2$ are preheated at 30° C. for 10 minutes and reactions started by adding enzyme. Reactions are quenched after 20 minutes with 40 uL of malachite green reagent (Promega). Phosphate released is then determined by measuring A650 and extrapolating the values to a phosphate standard curve. These methods are described in Rayapureddi, et al (2005) *Biochemistry* and Rayapureddi, et al., (2003) *Nature*, both incorporated in their entirety herein by reference.

Myelin Basic Protein (MyBP) Dephosphorylation Assay. The phosphatase activity of EYA toward MyBP substrates are measured using the Tyr phosphatase and Ser/Thr phosphatase assay kits from New England Biolabs. Briefly, 0.2 mM MyBP is tyrosine phosphorylated with either Abl kinase (for tyrosine phosphorylation) or cAMP-dependent protein kinase A [for Ser and Thr phosphorylation] in 50 mM Tris, pH 7.5, 10 mM MgCl2, 1 mM EGTA, 2 mM DTT, 0.01% Brij 35, 1 mM ATP, and 0.074 mCi of $\gamma$-$^{32}$P]-ATP. The phosphorylated proteins are purified as per the manufacturer's protocol. pY/S/T-MyBP (50 µM) are then treated with varying amounts of EYA in 20 mM MES, pH 5.5, and 2 mM $MgCl_2$. The samples are then electrophoresed on 15% SDS-PAGE gels and visualized by autoradiography.

Proliferation Assay. Cell proliferation is assayed by measuring the incorporation of 5-bromodeoxyuridine (BrdUrd) by immunofluorescence on cells labeled with 10 aM BrdUrd for 1-3 hours.

Cell Cycle Assay. This protocol is described in Zhang, 2005, incorporated herein in its entirety by reference.

In vivo Tumor Generation. This protocol is described in Zhang, 2005, incorporated herein in its entirety by reference.

Invasion/Migration assay. A modified Boyden assay is used to estimate the ability of Six and Eya to alter the invasiveness of tumor cell lines cells using Boyden chambers (BioCoat Becton-Dickinson, BD Biosciences, Palo Alto, Calif.) which consist of a 12-well cell culture plate with Matrigel® coated inserts tumor cell lines cells transfected with GFP, GFP-Eya, GFP-Six, or combinations of these plasmids are plated in the cell culture plate. Nicholson et al., *Transfilter Cell Invasion Assays*, 3$^{rd}$ ed.; *Cell Biology: A Laboratory Handbook* (2006) Elsevier Academic Press, pp. 359-362. After 48 hours the tops of the membranes are scraped to remove the plated cells, the membranes stained with Gills No. 1 hematoxylin, and the number of cells on the bottom of membranes counted to determine the relative percentage of cells that invaded through the transwell inserts (available from Corning).

Tumorogenicity assay. 8 week old nude mice are injected sub-cutaneously in the flank with tumor cell lines stably transfected with Six and/or Eya and/or mutant Eya as a control (lacking phosphatase activity). The tumor cells can be, for example, MDA-MB-231, MCF10a, MCF10a-Eya, MCF-10a-Six, MCF10a-Eya(mutant), or MCF10a-Eya+MCF10a-Six suspended in medium without serum and supplemented with estrogen pellets. Tumor size is monitored over a 6-week period.

Primary focus formation assay. Tumor lines such as MCF7 cells are transfected with either the GFP vector or a vector containing GFP and a Six/Eya protein or polypeptide. Forty-eight hours after transfection the cells are split and grown in medium containing 5% serum until confluent. The formation of foci is inspected visually after 2 weeks of culture in low serum. The development of foci indicates transformation of cells.

Phosphatase Inhibition. Specificity of selected compounds is then determined Compounds having a minimum $IC_{50}$ of about 10 uM is then tested for their specificity towards a predetermined Eya isoforms protein or fragment (such as the ED region) versus a set of representative classical PTPs such as, for example, PTP1B, HAD S/T P-ase, SHP1 and Ser/Thr phosphatases that use aspartate as a nucleophile.

Statistical Analyses

Potential leads can be evaluated by comparing the Z factor, as described by Zhang et al. (1999) *J Biomol Screen.* 4(2):67-73, incorporated herein by reference.

To identify compounds effective to treat or prevent proliferative disorders such as cancer, the following exemplary method can be used. One of skill in the art will readily recognize equivalents and variants of the described protocol which are intended to be within the scope of the disclosure.

A compound library of drug-like compounds, enriched for complex heterocyclic compounds with an average molecular weight of 350-400 Da, excluding compounds with functional groups known or predicted to be unstable or toxic, is used. The compounds are then subjected to a primary screen in which inhibition of Eya phosphatase activity is determined The Eya can bee the full-length protein or a fragment containing sufficient activity, such as a fragment being the ED region.

A compound library of drug-like compounds, enriched for complex heterocyclic compounds with an average molecular weight of 350-400 Da, excluding compounds with functional groups known or predicted to be unstable or toxic, is used. The compounds are then subjected to a primary screen in which inhibition of Eya phosphatase activity is determined in the presence of a Six protein or fragment. The Eya can be the full-length protein or a fragment containing sufficient activity, such as a fragment containing the ED region.

The protocol is substantially that described in references 4, 17 and 18. Eya phosphatase activity is measured using the model chromogenic substrate p-nitro-phenylphosphate (pNPP) as described. Compounds that inhibit Eya activity at least 80% are then re-tested in triplicate and confirmed hits will be used to obtain dose-response curves. To ensure data quality and assay robustness, the Z value is used. The Z value is based on the difference between the signal of the positive control (ie, no test compound) and that of the negative control (no Eya protein or polypeptide). The Z value incorporates the standard deviation of each signal. A Z value of 1.0 is considered perfect, and Z values above 0.5 are generally considered ideal for HTS. As such, test compounds having a Z value of greater than 0.5 are used in the secondary screen. In both the primary and secondary screen, every plate also contains three additional controls: 20 mM Na-o-vanadate (which inhibits Eya), 20 mM EDTA (which inhibits 100% of Eya activity) and 50 mM NaF (which inhibits Eya).

Validation

Compounds that satisfy the potency and specificity criteria (for example, at least approximately 70% inhibition and an $IC_{50}$ of at least 10 uM) are validated for their ability to inhibit Eya activity towards model tyrosine phosphorylated peptides and proteins (pY-myelin basic protein). In order to obtain IC50 values (inhibitor concentration yielding 50% inhibition) for structure-activity relationships, fractional activity of Eya (Y axis) is plotted as a function of inhibitor concentration (X axis). The data can then be fit using a standard four-parameter logistic nonlinear regression analysis.

Compounds are assayed for their effect on PTP1B phosphatase activity as a measure of specificity. Compounds which selectively inhibit Eya phosphatase activity compared to PTP1B phosphatase activity are identified as selective-Eya inhibitors and potential therapeutic agents for proliferative disorder. The methods used are those described in 8, 23, 24, incorporated herein by reference.

The hits are then subjected to secondary assays, such as phenotypic assays, for example, proliferation in vitro (described above) and determination of tumor size using tumorigenicity assays as described above. Test compounds which are effective in inhibiting proliferation in vitro or slowing or stopping tumor growth in vivo are then identified as candidates for lead optimization as known in the art.

Pharmaceutical Compositions

Another aspect of this invention is compositions that contain a safe and effective amount of a subject compound, or a pharmaceutically-acceptable salt thereof, and a pharmaceutically-acceptable carrier. As used herein, "safe and effective amount" means an amount of the subject compound sufficient to significantly induce a positive modification in the condition to be treated, but low enough to avoid serious side effects (at a reasonable benefit/risk ratio), within the scope of sound medical judgment. A safe and effective amount of the subject compound will vary with the age and physical condition of the patient being treated, the severity of the condition, the duration of the treatment, the nature of concurrent therapy, the particular pharmaceutically-acceptable carrier utilized, and like factors within the knowledge and expertise of the attending physician.

Preparing a dosage form is within the purview of the skilled artisan. Examples are provided for the skilled artisan, but are non-limiting, and it is contemplated that the skilled artisan can prepare variations of the compositions claimed.

In addition to the subject compound, the compositions of this invention contain a pharmaceutically-acceptable carrier. The term "pharmaceutically-acceptable carrier," as used herein, means one or more compatible solid or liquid filler diluents or encapsulating substances which are suitable for administration to a mammal The term "compatible", as used herein, means that the components of the composition are capable of being commingled with the subject compound, and with each other, in a manner such that any interactions do not substantially reduce the pharmaceutical efficacy of the composition under ordinary use situations. Preferably when liquid dose forms are used, the compounds of the invention are soluble in the components of the composition. Pharmaceutically-acceptable carriers are, of course, of sufficiently high purity and sufficiently low toxicity to render them suitable for administration to the mammal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the subject compound is basically determined by the way the compound is to be administered. If the subject compound is to be injected, the preferred pharmaceutically-acceptable carrier is sterile, physiological saline, with a blood-compatible suspending agent, the pH of which has been adjusted to about 7.4.

If the mode of administering the subject compound is perorally, the preferred unit dosage form is therefore tablets, capsules, lozenges, chewable tablets, and the like. Such unit dosage forms contain a safe and effective amount of the subject compound, which is preferably from about 0.01 mg to about 350 mg, more preferably from about 0.1 mg to about 35 mg, based on a 70 kg person. The pharmaceutically-acceptable carrier suitable for the preparation of unit dosage forms for peroral administration are well-known in the art. Tablets typically contain conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically containe one or more solid diluents disclosed above. The selection of carrier components depends on secondary considerations like taste, cost, and shelf stability, which are not critical for the purposes of this invention, and can be readily made by a person skilled in the art.

Peroral compositions also include liquid solutions, emulsions, suspensions, and the like. The pharmaceutically-acceptable carriers suitable for preparation of such compositions are well known in the art. Such liquid oral compositions preferably containe from about 0.001% to about 5% of the subject compound, more preferably from about 0.01% to about 0.5%. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel® RC-591, tragacanth and sodium alginate; typical wetting agents include lecithin and polysorbate 80; and typical preservatives include methyl paraben and sodium benzoate. Peroral liquid compositions can also contain one or more components such as sweeteners, flavoring agents and colorants disclosed above.

Other compositions useful for attaining systemic delivery of the subject compounds include sublingual and buccal dosage forms. Such compositions typically containe one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above can also be included.

Compositions can also be used to deliver the compound to the site where activity is desired: intranasal doses for nasal decongestion, inhalants for asthma, and eye drops, gels and creams for ocular disorders.

Preferred compositions of this invention include solutions or emulsions, preferably aqueous solutions or emulsions containing a safe and effective amount of a subject compound intended for topical intranasal administration. Such compositions preferably containe from about 0.001% to about 25% of a subject compound, more preferably from about 0.01% to about 10%. Similar compositions are preferred for systemic delivery of subject compounds by the intranasal route. Compositions intended to deliver the compound systemically by intranasal dosing preferably containe similar amounts of a subject compound as are determined to be safe and effective by peroral or parenteral administration. Such compositions used for intranasal dosing also typically include safe and effective amounts of preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfate and others; aromatic agents; viscosity adjustors, such as polymers, including cellulose and derivatives thereof, and polyvinyl alcohol and acids and bases to adjust the pH of these aqueous compositions as needed. The compositions can also containe local anesthetics or other actives. These compositions can be used as sprays, mists, drops, and the like.

Other preferred compositions of this invention include aqueous solutions, suspensions, and dry powders containing a safe and effective amount of a subject compound intended for atomization and inhalation administration. Such compositions preferably containe from about 0.1% to about 50% of a subject compound, more preferably from about 1% to about 20%; of course, the amount can be altered to fit the circumstance of the patient contemplated and the package. Such compositions are typically contained in a container with attached atomizing means. Such compositions also typically include propellants such as chlorofluorocarbons 12/11 and 12/114, and more environmentally friendly fluorocarbons, or other nontoxic volatiles; solvents such as water, glycerol and ethanol, these include cosolvents as needed to solvate or suspend the active; stabilizers such as ascorbic acid, sodium metabisulfite; preservatives such as cetylpyridinium chloride and benzalkonium chloride: tonicity adjustors such as sodium chloride; buffers; and flavoring agents such as sodium saccharin. Such compositions are useful for treating respiratory disorders, such as asthma and the like.

Other preferred compositions of this invention include aqueous solutions containing a safe and effective amount of a subject compound intended for topical intraocular administration. Such compositions preferably contain from about 0.0001% to about 5% of a subject compound, more preferably from about 0.01% to about 0.5%. Such compositions also typically include one or more of preservatives, such as benzalkonium chloride, thimerosal, phenylmercuric acetate; vehicles, such as poloxamers, modified celluloses, povidone and purified water; tonicity adjustors, such as sodium chloride, mannitol and glycerin; buffers such as acetate, citrate, phosphate and borate; antioxidants such as sodium metabisulfite, butylated hydroxy toluene and acetyl cysteine; acids and bases can be used to adjust the pH of these formulations as needed.

Other preferred compositions of this invention useful for peroral administration include solids, such as tablets and capsules, and liquids, such as solutions, suspensions and emulsions (preferably in soft gelatin capsules), containing a safe and effective amount of a subject compound. Such compositions preferably containe from about 0.01 mg to about 350 mg per dose, more preferably from about 0.1 mg to about 35 mg per dose. Such compositions can be coated by conventional methods, typically with pH or time-dependent coatings, such that the subject compound is released in the gastrointestinal tract at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit® coatings, waxes and shellac.

Pharmaceutically acceptable salt(s) include but is not limited to salts of acidic or basic groups that can be present in compounds identified using the methods of the present invention. Compounds that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds that include an amino moiety can form pharmaceutically or cosmetically acceptable salts with various amino acids, in addition to the acids mentioned above. Compounds that are acidic in nature are capable of forming base salts with various pharmacologically or cosmetically acceptable cations. Examples of such salts include alkali metal or alkaline earth metal salts and, particularly, calcium, magnesium, sodium lithium, zinc, potassium, and iron salts.

Any of the compositions of this invention can optionally include other drug actives.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art can develop equivalent means or reactants without the exercise of inventive capacity and without departing from the scope of the invention.

Example 1

Over-Expression of Eya3 Results in Increased Cell Proliferation

To examine the effect of Eyes Absent over-expression in cells, three independent clones expressing different levels of an Eya-GFP fusion protein were established. The human breast cancer cell line MCF-7 was cultured in Dulbecco's Modified Eagle Medium (DMEM) (Mediatech) supplemented with 10% fetal bovine serum and 1x antibiotic/antimycotic (Invitrogen). The MCF-7 cells were transfected with a mouse Eya3-GFP construct using Effectene® (Qiagen). The Eya3-GFP construct was generated from a full-length cDNA containing the sequence of the mouse Eya3 transcript variant 2 (NM_010166.2). Stable transfectant clones were established using G418 selection and screened for differential levels of expression by quantitative reverse transcriptase-polymerase chain reaction (qRT-PCR). Three clones, Eya3-GFP, Eya3-GFP #5, and Eya3-GFP #6, expressing relatively increasing levels of Eya3, as measured by qRT-PCR, were chosen for further study.

Figure 4:
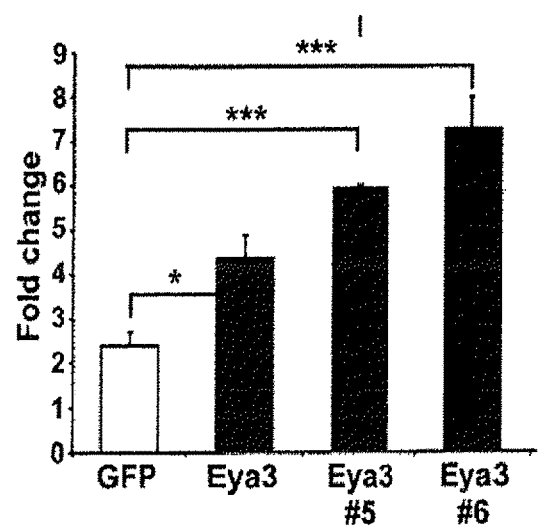
FIG. 4 is a graph of in vitro cell proliferation demonstrating increased cell number in cells over-expressing Eya3. The human breast cancer cell line MCF-7 was stably transfected with a DNA construct that expressed a mouse Eya3-GFP fusion transcript (GFP-green fluorescent protein). Cell proliferation was measured using a MTT assay among three separate clones, Eya3-GFP, Eya3-GFP#5 and Eya3-GFP#6, each expressing relatively increasing levels of Eya3. The clear bar is a vector control (GFP alone). Bars indicate fold-increase in number of viable cells 48 hours after the start of the experiment (mean±SD of six experiments; * $p<0.001$,  $p<0.01$, * $p<0.05$).

To determine the influence of Eya3 over-expression on cell proliferation, a MTT cell proliferation assay was conducted. Three clones expressing the Eya3-GFP fusion transcript, Eya3-GFP, Eya3-GFP #5, and Eya3-GFP #6, as well as MCF-7 transfectant line expressing GFP only (vector control), were grown separately in 10-cm dishes to 80% confluency, trypsinized and counted. Cells were diluted to 2000 cells/100 µl. and plated in 6 replicate wells of a 96-well tissue culture plate at a volume of 100 µl. (2000 cells/well). On day 1, two identical plates were set-up for initial cell and 48-hour time points. After cells attached to the initial count plate, 10 µl. of cell counting kit-8 (CCK-8) WST reagent (water-soluble tetrazolium salt-8) (Dojindo) was added to each well. The plate was incubated for 2 hours at 37° C. under normal tissue culture conditions. Absorbance at 450 nm was read on a Biotek plate reader. These readings were converted to cell number which was calculated from a standard curve using different numbers of MCF-7 cells. After 48 hours, the second plate was read in the same manner as the initial count plate. A fold change was calculated by dividing the number of cells at 48 hours by the number of cells on the initial plate. The results of this experiment are shown in FIG. 4. Over-expression resulted in a significantly increased dose-dependent cell proliferation. Bars indicate the fold-increase in the number of viable cells 48 hours after the start of the experiment (mean±SD of six experiments; * $p<0.001$,  $p<0.01$, * $p<0.05$).

Example 2

The Phosphatase Activity of Eya Promotes Cell Migration and Invasion

Characteristic cellular properties of malignant tumor cells include changes in cellular proliferation, migration and invasion. Also, cell migration is a response in angiogenesis. To examine the effect of Eya over-expression on cell migration, a transwell assay was utilized. The migration of MCF-7 cells expressing GFP, over-expressing Eya3 (Eya3-GFP and Eya3-GFP #6; described in Example 1), or a phosphatase deficient Eya3 mutant, Eya3(D246N)-GFP, were compared. Assays were preformed using transwell inserts (8 µm pore size polycarbonate membrane) in 24-well plates (Corning® Costar®). Typically, $5×10^4$ cells (100 µl per chamber) were grown in DMEM supplemented with 10% FBS and placed in the upper chamber. The lower chamber was loaded with 600 µl of DMEM supplemented with 10% FBS. After incubation for 24 hours at 37° C. with 5% $CO_2$, the top surface of each membrane was cleared of cells with a cotton swab. Cells that had penetrated to the bottom side of the membrane were fixed with methanol for 10 minutes and stained with Giemsa stain for 30 minutes and then counted. At least 10 microscopic fields were counted for each. Three independent experiments were performed.

MCF-7 cells over-expressing phosphatase sufficient forms of Eya3 (Eya3-GFP and Eya3-GFP#6) each exhibited significantly higher cell migration relative to MCF-7 cells expressing GFP alone. (FIG. 5A). The phosphatase-dead form of Eya, Eya3(D246N)-GFP consistently demonstrated attenuated cell migration compared to the phosphatase sufficient forms. Increased migration, due to over-expression of Eya3, occurred independently of the underlying cell line chosen, since MDA-MB-231 cells, another human breast cancer line, transfected with the Eya3 constructs, showed a similar migration profile. (FIG. 5A). Each bar represents the mean of three experiments±SD, * $p<0.001$,  $p<0.01$, * $p<0.05$. Eya3 (D246N)-mutation from aspartic acid to asparagine at amino acid position 246 of Eya3.

The invasive potential of MCF-7 and MDA-MB-231 cells expressing either Eya3, Eya3(D246N) or GFP was measured using transwells coated with Matrigel™. The Matrigel™ invasion assays were performed, in nearly the same manner as the migration assay described above, with the exception that the transwells were coated with basement membrane Matrigel™ (BD Biosciences) diluted 1:20 and the cells migrating to the bottom side of the insert were measured 48 hours after the start of the experiment. Each bar represents the mean of three experiments±SD, * $p<0.001$,  $p<0.01$, * $p<0.05$. (FIG. 5B). In each case, there was a clear increase in the invasiveness upon Eya3 over-expression that was significantly lower when Eya3(D246N) was over-expressed.

Example 3

Interaction with SIX 2 or SIX6 Increases the Tyrosine Phosphatase Activity of Eya3

The Eyes Absent proteins interact with the SIX family of homeodomain transcription factors. Whether the interaction of Eyes Absent and SIX family members has an affect on the enzymatic activity of EYA was tested. These experiments were conducted with Eya3 and representatives of two distinct classes of SIX proteins; SIX2 and SIX6. The ability of Eya3 to dephosphorylate the tyrosine-phosphorylated peptide derived from H2AX was monitored in the presence or absence of stoichiometric amounts of either SIX2 or SIX6.

Recombinant, purified proteins were used in these experiments. To obtain the SIX proteins, human six6 and mouse six2 cDNA were obtained from ATCC (American Type Culture Collection) and used as templates for PCR. The coding sequences for six6 and six2 were inserted into the vector pDEST527 (Invitrogen) by recombinational cloning using the Gateway® cloning system (Invitrogen). A cleavage site for Tobacco vein mottling virus (TVMV) protease was inserted between the His-tag and the protein coding sequences. The resulting expression vector was transformed into E. coli strain BL21 (DE3), grown at 37° C. in Luria broth and induced with isopropyl β-D-1-thiogalactopyranoside (IPTG). These cells were lysed in 20 mM tris pH 8.0, 0.5M NaCl, 5 mM imidazole and 1% triton X-100, loaded on a Ni-NTA column and eluted with increasing concentrations of imidazole. Fractions containing the His-tagged proteins were dialyzed against 20 mM Tris pH 8, 300 mM NaCl and treated with TVMV protease for 12 hours at 4° C. The cleaved proteins were then further purified by size-exclusion chromatography on a Superdex-200 column.

Nucleotides encoding full-length Eya3 were inserted into pGEX-4T using conventional PCR cloning methods. The resulting vector was transformed into BL21(DE3), grown in Luria broth, and induced with IPTG at room temperature. Cells were lysed in 20 mM Tris pH 8, 150 mM NaCl, 1% Triton X-100. The lysis supernatant was applied to glutathione agarose beads, the column was washed extensively with the lysis buffer and the protein was released from the GST-tag by thrombin treatment in 20 mM Tris pH 8, 150 mM NaCl. Thrombin was inhibited by 10 mM benzamidine. Eya3 was further purified by anion exchange chromatography (Fast Q) and eluted with an NaCl gradient at pH 8. PAGE purified DNA oligonucleotides were obtained from Integrated DNA Technologies. Synthetic peptides were obtained from Genscript.

Phosphatase assays using a tyrosine phosphorylated peptide, the histone H2AX C-terminus peptide (KKATQASQEpY, SEQ ID NO. 7), as a substrate was conducted as described. Rayapureddi et al. (2003) Nature 426: 295-298; Rayapureddi and Hegde (2006) FEBS Lett. 580: 3853-3859. Eya3 enzyme or its various complexes were added and incubated for 20 minutes.

For peptide assays, reaction mixtures (50 µl) with different concentrations of phosphopeptides were preheated at 30° C. (or 37° C.) for 10 min. and reactions started by adding enzyme. Reactions were quenched after 20 min. (or 60 min. for assays with the pT-peptide) with 100 µl of Biomol reagent (Enzo Life Sciences Inc.). Phosphate released was determined by measuring absorbance at 630 nm and extrapolating the values to a phosphate standard curve. All results were analyzed using PRISM® (Graphpad Software).

To assay phosphatase activities towards tyrosine phosphorylated proteins NIH293T cells were used as a source of susbtrate. Cells were grown to confluence, treated for 15 minutes with 0.1 mM Na-o-vanadate and 0.03% hydrogen peroxide, and lysed with 10 mM Tris pH 7.6, 150 mM NaCl, 10 mM $MgCl_2$, 1% Triton X-100, 1 mM Na-ortho-vanadate, 1 mM DTT, 1 mM PMSF, and protease inhibitor cocktail (Sigma). Protein concentration of the cell lysate was estimated by Biorad assay. Cell lysates were treated with recombinant Eya3 or Eya3(ED) in 50 mM MES pH 6, 100 mM NaCl, and 10 mM $MgCl_2$ containing buffer for 30 minutes at 30° C. The reaction mixtures were then loaded on SDS-PAGE gels, transferred to nitrocellulose membrane and probed with monoclonal anti-phosphotyrosine antibody (Santa Cruz Biotechnology).

The interaction with these SIX proteins increases the $k_{cat}$ of Eya3, while the $K_m$ values remain relatively similar. (FIG. 6A) In control experiments neither SIX2 nor SIX6 showed any catalytic activity and the presence of SIX2 or SIX6 did not alter the inability of Eya3 to dephosphorylate either pNPP or phosphotyrosine.

Example 4

Interaction with DNA Further Increases the Tyrosine Phosphatase Activity of Eya3

In the nucleus, EYA-SIX complexes can interact with DNA. Furtheimore, the EYA substrate H2AX forms part of the nucleosome core particle. A C-terminal tyrosine of H2AX can be dephosphorylated by EYA. To confirm that an EYA-SIX-DNA complex retains the activity and specificity observed for the EYA-SIX complex, phosphatase assays were conducted in the presence of oligonucleotides known to bind SIX2. SIX2 binds specifically to the TCAGGTT (SEQ ID NO. 3) sequence present in the myogenin promoter. The catalytic activity of EYA3 compared to EYA3:SIX2, in the presence of the 12-mer containing the myogenin sequence (TGTCAGGTTGCT; myoDNA, SEQ ID NO. 8), a 12-mer containing an ATTA sequence in the context of the myogenin sequence (TGTGGATTAGCT; attaDNA, SEQ ID NO. 9) and a completely unrelated DNA sequence (nsDNA), was compared. (FIG. 6B).

That there is specific DNA binding by the EYA-SIX complex is shown in FIG. 6(C). The presence of an oligonucelotide, that can be specifically bound by SIX, increases the efficiency of the dephosphorylation of the terminal tyrosine of H2AX.

Example 5

A Vitual Screening of Inhibitors of the Eyes Absent Phosphatase Activity

In silico chemical library screening or virtual screening (also known as high through-put docking or high through-put virtual screening; Walters et al. (1998) Drug Discovery Today 3:160-178) was used to identify compounds that bind to the ED domain of Eya3. To generate a model of Eya3(ED) the crystal structure of Eya2(ED)(3GEB.PDB; Protein Data Bank) was used as a template and the SWISSMODEL server. Structure-based alignment of residues 238-509 of Eya3 with residues 267-537 of Eya2(ED) was used. The resulting homology model was validated using ANOLEA, VERIFY-3D and GROMOS. These analyses indicated that the molecular geometry of the model was of good quality.

Figure 7:
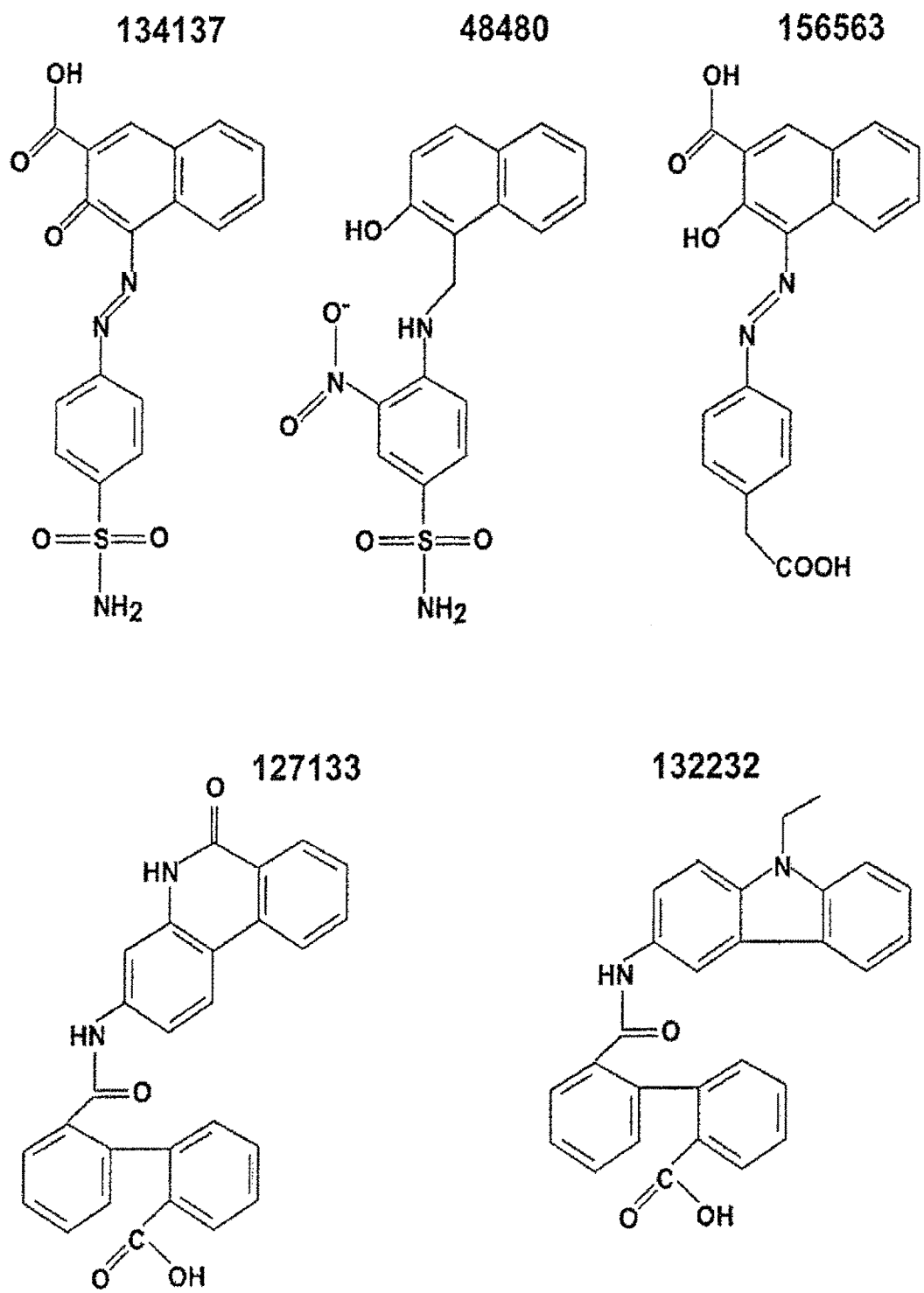
FIG. 7 shows the structures of two classes of compounds that show inhibition of Eya3 catalytic activity in vitro.

The virtual screen was carried out utilizing the NCI Diversity Set II library of small molecules. Compounds identified with a predicted binding affinity in the nanomolar range were then tested for their ability to inhibit the phosphatase activity of Eya3 (ED) towards pNPP. The classes of compounds that emerged from this screen and are shown in FIG. 7. These compounds have a IC50 ranging from 26-39 µM.

Example 6

Lead Compounds

Figure 8:
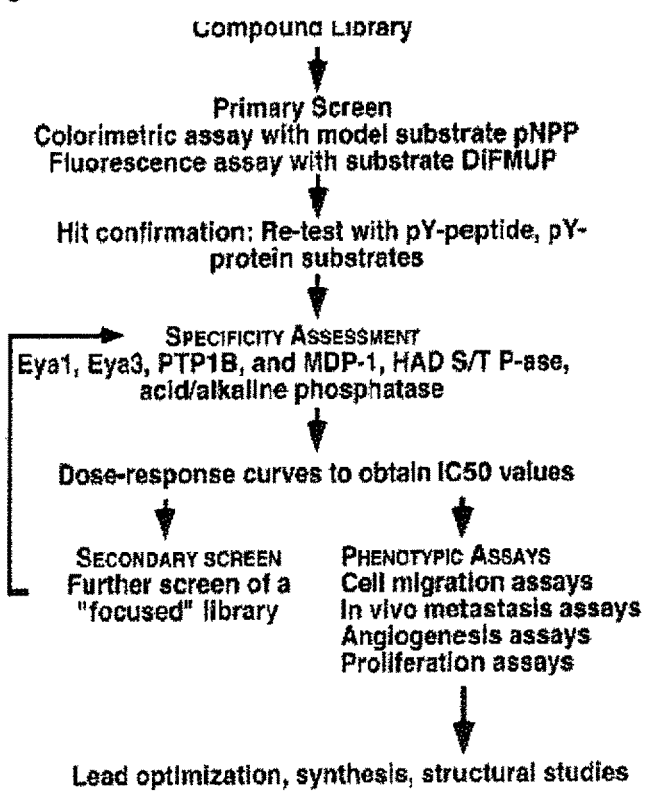
FIG. 8 is a flow diagram illustrating lead optimization protocol beginning with a compound library.

The following classes of compounds were identified by a virtual screen as lead compounds:

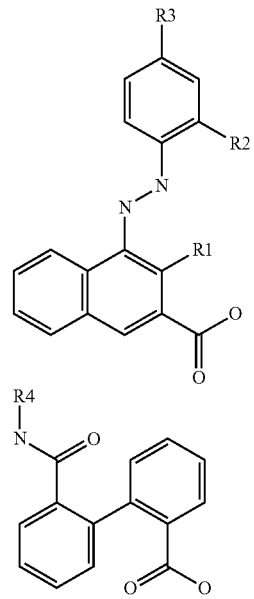

Where R1 can be: a hydroxyl, an oxo, a nitro, and/or an amino group. R2 and R3 can be: a sulfo, a sulfonylamino, a diaminomethylideneaminosulfonyl, a sulfamoyl, a hydrozyalkyl, a carboxyalkyl, an alkoxycarbonyl, a carbomyl, a dialkylcarbamoyl and/or an alkylaminosulfonylakyl group. R4 can be: a saturated or unsaturated cyclic 5 or 6 membered hydrocarbon that is substituted or unsubstituted; a saturated or unsaturated cyclic 5 or 6 member heterocycle that is substituted or unsubstituted; a saturated or unsaturated dicyclic fused ring that is substituted or unsubstituted; and/or a saturated or unsaturated tricyclic fused ring that is substituted or unsubstituted. These compounds are the subject of further analysis as outlined in FIG. 8. These compounds can be modified to generate an appropriate Eya agonist or antagonist.

Example 7

Eya3 Possess Potent Angiogenesis-Like Activity

Figure 9:
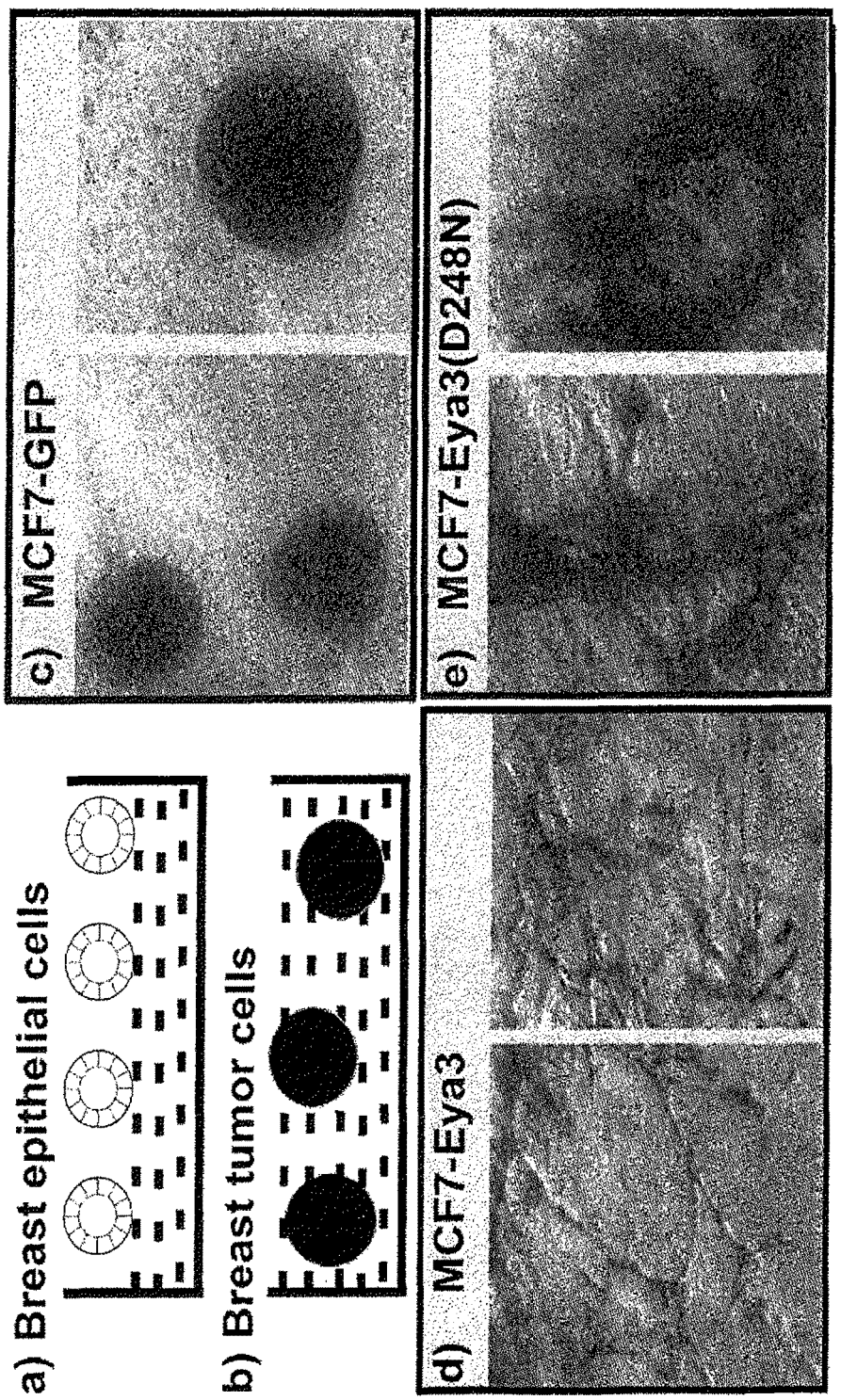
FIG. 9 shows that Eyes Absent expression in MCF-7 cells promotes the formation of branched cellular structures. Formation of branched networks in cultured cells can be indicative of angiogenic stimulation. (A) Normal breast epithelium cells, when cultured, form polarized spheres typical of the mammary gland acini. (B) In contrast, breast tumor cells, such as MCF-7, form large, dense, unpolarized colonies of cells. (C) MCF-7 cells expressing GFP, showing the large, dense, unpolarized colonies of cells typical of MCF-7 cells. (D) MCF-7 cells over-expressing Eya3-GFP form branched structures. (E) MCF-7 cells expressing the phosphatase-deficient Eya3(D246N)-GFP are less able to form the branched network seen in (D).

Eya3 expression induces a morphological transformation in MCF-7 cells plated in Matrigel®. In this assay, cells are plated in Matrigel®, a biologically active basement membrane model) and incubated at 37° C. MCF cells were transfected with Eya3, Eya3(D246N) or GFP. Stably transfected clones were plated in Matrigel®. MCF-7 cells stably overexpressing Eya3 were observed to form a branched network, while those cells expressing GFP alone failed to undergo this morphological change. FIG. 9. Human endothelial cells undergoing angiogenic stimulation also form branched networks. Cells expressing the phosphatase-deficient mutant of Eya3 (D246N), were much less likely to form these branched networks.

Example 8

Anti-Angiogenesis Activity of a Specific Inhibitor of Eya Activity

A candidate compound, an Eyes Absent inhibitor, is tested for its ability to regulate angiogenesis. The aortic ring assay is an established method for assessing angiogenic modulators. In this assay, aortic ring explants are established in a collagen gel that is polymerized within cylindrical agarose wells cast into a 60 mm tissue culture plate. This arrangement provides triplicate explants in a single dish. The dish is provided with standard tissue culture medium. Angiogenic stimuli is placed in the agarose, providing a concentration gradient to the explant.

Three concentrations of the test compound are diluted in culture medium and applied to the culture plates. Dishes without the Eyes Absent inhibitor serve as controls. Culture medium is replenished twice, at days 2 and 4, during the 6 day time course of the assay. Quantification of the angiogenic responses in the aortic ring assay are performed by counting the number of sprouts emerging from the explant. A reduction in the number of sprouts within a given field is indicative of an inhibition in angiogenesis and a positive response.

Alternatively, a candidate compound, an Eyes Absent inhibitor, is tested for its ability to regulate angiogenesis by pupillary membrane angiogenesis assay. Soon after birth, the pupillary membrane vessels begin a process of regression. Injection of angiopoietin 2 (Ang2) results in angiogenesis, including the formation of vessel sprouts.

In this assay, the left eye of a mouse pup is injected with Ang2 with or without the test compound. The degree of angiogenic response is quantified by counting (1) angiogenic sprouts and (2) the number of migrating VECs. This is accomplished by labeling hyaloid preps for the VEC-specific junctional marker VE-cadherin and then counting VECs that are in sprouts or have migrated away from pre-existing vessels. Since normal hyaloid has none of these cells, the angiogenic response is simple to quantify.

A reduction in the number of sprouts, in mice treated with the inhibitor, for example, is indicative of an inhibition of angiogenesis.

The various methods and techniques described above provide a number of ways to carry out the invention. Of course, it is to be understood that not necessarily all objectives or advantages described need be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several advantageous features, while others specifically exclude one, another, or several features, while still others specifically mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications is herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A method for identifying a potential therapeutic agent for the treatment of a disorder associated with Eyes Absent dysregulation, comprising the steps of:
   i) providing an Eya protein or fragment thereof, wherein the Eya protein or fragment possesses relevant biochemical activity, and a substrate capable of being dephosphorylated by the Eya protein or fragment;
   ii) delivering a test molecule to the Eya protein or fragment, wherein the test molecule is a small molecule, peptide, polypeptide, or antibody;
   iii) determining the effect of the test molecule on the phosphatase activity of the Eya protein or fragment; and
   iv) comparing the phosphatase activity of the Eya protein or fragment in the presence of a test molecule to that of a reference standard;
   wherein a test molecule that increases or decreases Eya phosphatase activity is a potential therapeutic agent for the treatment of a disorder associated with Eya dysregulation.

2. The method of claim 1, further comprising the steps of:
   i) providing a Six protein or fragment thereof, wherein the Six protein or fragment possesses relevant biochemical activity; and
   ii) delivering a test molecule to the Six protein or fragment, wherein the test molecule is a small molecule, peptide, polypeptide, or antibody.

3. The method according to claim 1 wherein the disorder associated with Eya dysregulation is a proliferative disorder.

4. The method according to claim 1 wherein the disorder associated with Eya dysregulation is an invasive and/or metastatic disorder.

5. The method according to claim 1 wherein the disorder associated with Eya dysregulation is a angiogenic disorder.

6. The method according to claim 1 wherein the disorder associated with Eya dysregulation is a vascular disorder.

7. The method according to claim 1 wherein the disorder associated with Eya dysregulation is cancer.

8. The method according to claim 1 wherein the Eya protein is selected from the group consisting of Eya1, Eya2, Eya3 and Eya4.

9. The method according to claim 1 wherein the fragment includes the ED region of an Eya protein selected from the group consisting of Eya1, Eya2, Eya3, and Eya4.

10. The method according to claim 2 wherein the Six protein is selected from the group consisting of Six1, Six2, Six3, Six4, Six5, and Six6.

11. The method according to claim 1 wherein the substrate is selected from the group consisting of the model substrate pNPP, phospho-amino acids, phosphorylated peptides or phosphorylated proteins.

* * * * *

UNITED STATES PATENT AND TRADEMARK OFFICE
CERTIFICATE OF CORRECTION

PATENT NO.        : 8,486,651 B2
APPLICATION NO. : 13/133593
DATED             : July 16, 2013
INVENTOR(S)       : Rashmi Hegde It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 33 days.

Signed and Sealed this
Eighth Day of September, 2015

Michelle K. Lee
*Director of the United States Patent and Trademark Office*